US012773551B2

(12) United States Patent
Katsanos et al.

(10) Patent No.: US 12,773,551 B2
(45) Date of Patent: Oct. 27, 2026

(54) NEUROMODULATION TO ENHANCE PHYSICAL ACTIVITY BEHAVIOR

(71) Applicants: Christos Katsanos, Phoenix, AZ (US); Anaissa Ruiz Tejada, Scottsdale, AZ (US)

(72) Inventors: Christos Katsanos, Phoenix, AZ (US); Anaissa Ruiz Tejada, Scottsdale, AZ (US)

(73) Assignee: Arizona Board of Regents of behalf of Arizona State University, Scottsdale, AZ (US)

( * ) Notice: Subject to any disclaimer, the term of this patent is extended or adjusted under 35 U.S.C. 154(b) by 433 days.

(21) Appl. No.: 18/324,228

(22) Filed: May 26, 2023

(65) Prior Publication Data

US 2023/0381495 A1 Nov. 30, 2023

Related U.S. Application Data

(60) Provisional application No. 63/346,549, filed on May 27, 2022.

(51) Int. Cl.

| | |
|---|---|
| ***A61N 1/04*** | (2006.01) |
| ***A61B 5/11*** | (2006.01) |
| ***A61N 1/20*** | (2006.01) |
| ***A61N 1/36*** | (2006.01) |

(52) U.S. Cl.

CPC .......... *A61N 1/0456* (2013.01); *A61B 5/1118* (2013.01); *A61N 1/0484* (2013.01); *A61N 1/20* (2013.01); *A61N 1/36034* (2017.08)

(58) Field of Classification Search

CPC .. A61N 1/0456; A61N 1/0484; A61N 1/0526; A61N 1/36034

See application file for complete search history.

(56) References Cited

U.S. PATENT DOCUMENTS

| | | | | |
|---|---|---|---|---|
| 2016/0360990 A1* | 12/2016 | Altshuler | ............. | A61B 5/6803 |
| 2018/0168905 A1* | 6/2018 | Goodall | ............... | A61B 5/1124 |

OTHER PUBLICATIONS

"Neuromodulation to Enhance Physical Activity Behavior: Arizona Technology Enterprises." Mar. 8, 2023, skysong. technologypublisher. com/tech/Neuromodulation_to_Enhance_Physical_Activity_ Behavior.

Abizaid et al., The Journal of clinical investigation, 116(12), 3229-3239.

Agarwal, International journal of general medicine. 2012;5:541-5.

(Continued)

*Primary Examiner* — Alyssa M Alter

(74) *Attorney, Agent, or Firm* — Riverside Law LLP

(57) ABSTRACT

A device for neurostimulation having an extendable headband having first and second arms each having a proximal end and a distal end, the two arms connected to one another at the proximal ends via an extension mechanism, an electrode band having first and second ends, the first end rotatably connected to a point on the first arm, and the second end rotatably connected to a point on the second arm, and first and second electrodes slidably positioned on the electrode band configured to deliver neurostimulation to a subject. A method of encouraging a behavior of a subject, for example physical activity, is also described.

22 Claims, 21 Drawing Sheets

(56) References Cited

OTHER PUBLICATIONS

American College of Sports Medicine Annual Meeting & World Congresses Proceedings (San Diego, CA, May/Jun. 2022). Abstract Title: "Effects of Transcranial Direct Current Stimulation on Physical Activity Levels in Healthy Subjects: A Pilot Study"—May 31-Jun. 4, 2022.
American College of Sports Medicine Annual Meeting & World Congresses Proceedings (San Diego, CA, May/Jun. 2022). Abstract Title: "Effects of Transcranial Direct Current Stimulation on Physical Activity Levels in Healthy Subjects: A Pilot Study"—May 31-Jun. 4, 2022. (Abstract).
Amin, F., Michael, D., & Davis, K. L. (1992). Schizophrenia Bulletin, 18(1), 123-148.
Angius et al., Frontiers in physiology. 2017;8:90.
Arizona Physiological Society Annual Meeting Proceedings (Glendale, AZ, Nov. 2021). Abstract Title: "Effects of Transcranial Direct Current Stimulation on Physical Activity and Intrinsic Motivation towards Exercise"—Oct. 29-30, 2021.
Arizona Physiological Society Annual Meeting Proceedings (Glendale, AZ, Nov. 2021). Abstract Title: "Effects of Transcranial Direct Current Stimulation on Physical Activity and Intrinsic Motivation towards Exercise"—Oct. 29-30, 2021 (Abstract).
Arizona Physiological Society Annual Meeting Proceedings (Virtual Meeting, Nov. 2020). Abstract Title: "Transcranial Direct Current Stimulation to Enhance Physical Activity Behavior: A Methodology Abstract"—Nov. 5-6, 2020.
Arizona Physiological Society Annual Meeting Proceedings (Virtual Meeting, Nov. 2020). Abstract Title: "Transcranial Direct Current Stimulation to Enhance Physical Activity Behavior: A Methodology Abstract"—Nov. 5-6, 2020 (Abstract).
Bacopoulos et al., European Journal of Pharmacology, 56(3), 225-236.
Bherer et al., Journal of aging research. 2013;2013:657508.
Bredland et al., BMC Public Health. 2018; 18(1):627.
Brunoni et al., Brain stimulation. 2012;5(3):175-95.
Buman et al., Am J Epidemiol. 2014;179(3):323-34.
Cheval et al., Sports Med. 2018;48(6):1389-404.
Cid, Luis, et al. (2018). Frontiers in Psychology, 9; 1940-1940.
Colberg et al., Assoc. Diabetes Care. 2016;39(11):2065-79.
Duncan, L.R., Hall, C.R., Wilson, P.M et al. (2010). Int J Behav Nutr Phys Act. 7-7.
Dutta et al., Sensors. 2018;18(11).
Fishman, Ezra I., et al. (2016). American College of Sports Medicine, 48-7; 1303-11.
Floegel et al., Geriatr Nurs. 2018. PubMed PMID: 30391041.
Foldvary-Schaefer, Nancy & Grigg-Damberger, Madeleine. (2012). Sleep Medicine Clinics. 7. 39-58. 10.1016/j.jsmc.2012.01.002.
Fonteneau et al., Cereb Cortex. 2018;28(7):2636-46.
Friend et al., Cell Metab. 2017;25(2):312-21.
Fukai, M. (2019). Endogenous dopamine release under transcranial direct-current stimulation governs enhanced attention: A study with positron emission tomography. 10. 6.
Fulton et al., Neuron, 51(6), 811-822.
Garland et al., J Exp Biol. 2011;214(Pt 2):206-29.
Hall et al., Appetite. 2018; 124:78-88.
Heinitz et al., Am J Clin Nutr. 2017; 106(6):1347-57.
Hsu et al., J Neurosci. 2014;34(34):11366-84.
Jang et al., Experimental neurobiology. 2017;26(2):104-12.
Janssen & Leblanc, The international journal of behavioral nutrition and physical activity. 2010;7:40.
Jiang et al., Molecular endocrinology, 20(8), 1772-1785.
Knab & Lightfoot, International journal of biological sciences. 2010;6(2):133-50.
Knab et al., Behav Brain Res. 2009;204(1):147-52.
Knab et al., J Biol Regul Homeost Agents. 2012;26(1):119-29.
Larouche et al., Frontiers in public health. 2018;6:323.
Lattari et al., Neurosci Lett. 2018;662:12-6.
Lavie, Carl, et al. (2019) Circulation Research, 124-5; 799-815.
Marshall AL. J Sci Med Sport. 2004;7(1 Suppl):60-6.
Matthews et al., Am J Epidemiol. 2008; 167(7):875-81.
Mogenson et al., Prog Neurobiol. 1980; 14(2-3):69-97.
Neurocare "DC-STIMULATOR." https://www.neurocaregroup.com/neuroconn-dc-stimulator. Accessed on Mar. 28, 2022.
Okano et al., Br J Sports Med. 2015;49(18):1213-8.
Oswald et al., Neuropsychopharmacology, 30(4), 821-832.
Park et al., Physiol Behav. 2016; 164(Pt A):383-9.
Piercy et al., JAMA. 2018;320(19):2020-8.
Roberts et al., (2012). Physiology & Behavior, 105(3), 661-668.
Ruegsegger & Booth, Frontiers in endocrinology. 2017;8:109.
Ruiz-Tejada A, Neisewander J, Katsanos CS. Brain Sciences. 2022; 12(3):333.
Ryan & Deci (2000). American Psychologist, 55-1; 68-78.
Salamone & Correa, Neuron. 2012;76(3):470-85.
Strazdins et al., Health Promot Int. 2011;26(1):46-54.
Sussman S, Lisha N, Griffiths M. Eval Health Prof. 2011;34(1):3-56.
Swift et al., Prog Cardiovasc Dis. 2014;56(4):441-7.
Tran et al., Proc Natl Acad Sci U S A. 2005; 102(6):2117-22.
Troiano et al., Medicine & Science in Sports & Exercise, 40(1), 181-188.
Vega-López et al., BMC Research Notes, 7(1), 29. https://doi.org/10.1186/1756-0500-7-29.
Warburton & Bredin, Curr Opin Cardiol. 2017;32(5):541-56.
Yamamoto et al., eNeurologicalSci. 2017;7:1-6.

* cited by examiner

| | SS | DF | MS | F (DFn, DFd) | *P* |
|---|---|---|---|---|---|
| TIME x GROUP | 2.32 | 1 | 2.32 | F (1, 28) = 4.43 | 0.04 |
| TIME | 0.18 | 1 | 0.18 | F (1, 28) = 0.34 | 0.57 |
| GROUP | 0.03 | 1 | 0.03 | F (1, 28) = 0.02 | 0.89 |

NEUROMODULATION TO ENHANCE PHYSICAL ACTIVITY BEHAVIOR

CROSS-REFERENCE TO RELATED APPLICATIONS

This application claims priority to U.S. Provisional Application No. 63/346,549, filed on May 27, 2022, incorporated herein by reference in its entirety.

BACKGROUND OF THE INVENTION

There is plethora of evidence showing that physical activity increases overall quality of life by reducing the risk of cardiovascular and metabolic diseases, including Type II diabetes and obesity (Colberg et al., Assoc. Diabetes Care. 2016; 39(11):2065-79; Agarwal, International journal of general medicine. 2012; 5:541-5; Warburton & Bredin, Curr Opin Cardiol. 2017; 32(5):541-56; Swift et al., Prog Cardiovasc Dis. 2014; 56(4):441-7; Bherer et al., Journal of aging research. 2013; 2013:657508). The Physical Activity Guidelines for Americans 2018 (Piercy et al., JAMA. 2018; 320(19):2020-8), recommend that adults should participate in 150-300 minutes of moderate-intensity or 75-150 min of vigorous-intensity physical activity weekly. Despite such recommendations for physical activity, however, less than 5% of adults over 20 years of age engage in at least 30 mins of moderate physical activity daily (Piercy et al., JAMA. 2018; 320(19):2020-8). Incorporating enough physical activity or exercise in daily life is a challenge for the majority of people.

Regulation of voluntary motor action and motivation for physical activity is the result of brain mechanisms related to cognition, reward, and habit, and which are linked to the dopamine system (Garland et al., J Exp Biol. 2011; 214(Pt 2):206-29; Mogenson et al., Prog Neurobiol. 1980; 14(2-3):69-97; Cheval et al., Sports Med. 2018; 48(6):1389-404). Studies using transgenic mice provide evidence for areas in the brain (i.e., striatum) that control the desire to exercise or to perform locomotor activity (Tran et al., Proc Natl Acad Sci USA. 2005; 102(6):2117-22; Ruegsegger & Booth, Frontiers in endocrinology. 2017; 8:109). Therefore, it is key to discover interventions that have the potential to modulate areas of the brain that control voluntary physical activity and in any effort to enhance physical activity and exercise behavior in people, as well as help people to adhere to exercise programs and physical activity.

Transcranial direct current stimulation (tDCS) involves neuromodulation of the brain. This procedure involves the application of low-intensity, direct, current to areas of the brain facilitating or inhibiting spontaneous neural activity. tDCS has been intensively investigated over the last decade in association with various brain disorders (i.e., depression, pain, drug addiction), with encouraging results (Brunoni et al., Brain stimulation. 2012; 5(3):175-95). It has been shown that neuromodulation of the brain modifies eating behavior/reduces food cravings (Hall et al., Appetite. 2018; 124:78-88), and tDCS applied to dorsolateral prefrontal cortex (DLPFC), reduces hunger/snack food intake in humans (Heinitz et al., Am J Clin Nutr. 2017; 106(6):1347-57). Application of neuromodulation in sports shows that tDCS improves exercise performance and reduces the perceived effort of exercise (Okano et al., Br J Sports Med. 2015; 49(18):1213-8; Angius et al., Frontiers in physiology. 2017; 8:90), while it enhances exercise tolerance (Lattari et al., Neurosci Lett. 2018; 662:12-6).

Current evidence from animal models shows that the mesolimbic dopamine system, and more precisely the ventral striatum/nucleus accumbens (NAc), plays important role in determining voluntary physical activity behavior (Knab et al., Behav Brain Res. 2009; 204(1):147-52; Knab & Lightfoot, International journal of biological sciences. 2010; 6(2):133-50; Knab et al., J Biol Regul Homeost Agents. 2012; 26(1):119-29), and that the NAc is also key in coordinating behavior at it relates to motivation (Salamone & Correa, Neuron. 2012; 76(3):470-85). Details on how these brain centers and relevant processes regulate specifically spontaneous, voluntary physical activity have been previously reviewed (Knab & Lightfoot, International journal of biological sciences. 2010; 6(2):133-50).

Thus, there is a need in the art for a non-invasive intervention protocol using tDCS technology that stimulates the dopaminergic pathways of the brain, in order to increase physical activity and/or exercise behavior. In addition, there is the need for a device that will aid in the set up of electrodes and facilitate the application of any tDCS protocol. The present invention satisfies such needs.

SUMMARY OF THE INVENTION

Aspects of the present invention relate to a device for positioning one or more neurostimulation electrodes on a subject, having an extendable headband including first and second arms each having a proximal end and a distal end, the two arms connected to one another at the proximal ends via an extension mechanism, an electrode band having first and second ends, the first end rotatably connected to a point on the first arm, and the second end rotatably connected to a point on the second arm, and first and second electrodes slidably positioned on the electrode band configured to deliver neurostimulation to the subject.

In some embodiments, the headband has telescopically inter-engaged components. In some embodiments, the first and second electrodes are selected from flexible sponge electrodes, rubber electrodes, pad electrodes, or bare electrodes. In some embodiments, the first electrode is an anode and the second electrode is a cathode. In some embodiments, the anode is positioned in proximity to a first position on the head of the subject, and the cathode is positioned in proximity to a second position on the head of the subject. In some embodiments, the first position is the left dorsolateral prefrontal cortex, and the second position is the right dorsolateral prefrontal cortex.

In some embodiments, the device is configured to provide a stimulus to the subject to encourage physical activity. In some embodiments, the device further includes an activity sensor configured to track the activity of the subject. In some embodiments, the electrodes connect to a neurostimulator device. In some embodiments, the device further includes a computing device with a power source.

Aspects of the present invention relate to a method of encouraging a behavior of a subject, having the steps of positioning one or more electrodes on a subject, providing a stimulus to the subject related to the behavior, providing neuromodulation or neurostimulation to the subject via the one or more electrodes in conjunction with the stimulus.

In some embodiments, the electrodes are positioned over the right and left dorsolateral prefrontal cortex. In some embodiments, the neuromodulation or neurostimulation includes a transcranial direct current stimulation (tDCS). In some embodiments, the tDCS includes an applied current of 1-6 mA for a duration of 1-45 minutes. In some embodiments, the stimulus includes an audio or visual stimulus. In some embodiments, the stimulus is a representation or the subject's execution of aerobic or resistance exercise, and wherein the behavior is increased physical activity.

In some embodiments, the method further includes the step of positioning a head-mounted device having a headband and electrode band on the head of the subject, the electrode band configured to position the one or more electrodes in contact with the head of the subject. In some embodiments, the method further includes the step of adjusting at least one dimension of the head-mounted device to conform to the size of the subject's head.

Aspects of the present invention relate to a method of encouraging a behavior of a subject, including the steps of providing any disclosed neurostimulator device of the present invention, positioning the first and second electrodes on the head of the subject, and providing neuromodulation or neurostimulation to the subject via the first and second electrodes.

In some embodiments, the method further includes the step of providing a stimulus to the subject related to the encouraged behavior. In some embodiments, the first electrode is positioned in proximity to a first position on the head of the subject, and the second electrode is positioned in proximity to a second position on the head of the subject. In some embodiments, the first position is the left dorsolateral prefrontal cortex, and the second position is the right dorsolateral prefrontal cortex.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 19A shows the comparison between BSL-INT. FIG. 19B shows the comparison between INT-FUP.

FIG. 20A and FIG. 20B show the results for the comparison between BSL-INT. FIG. 20C and FIG. 20D show the comparison between INT-FUP.

DETAILED DESCRIPTION

Figure 1:
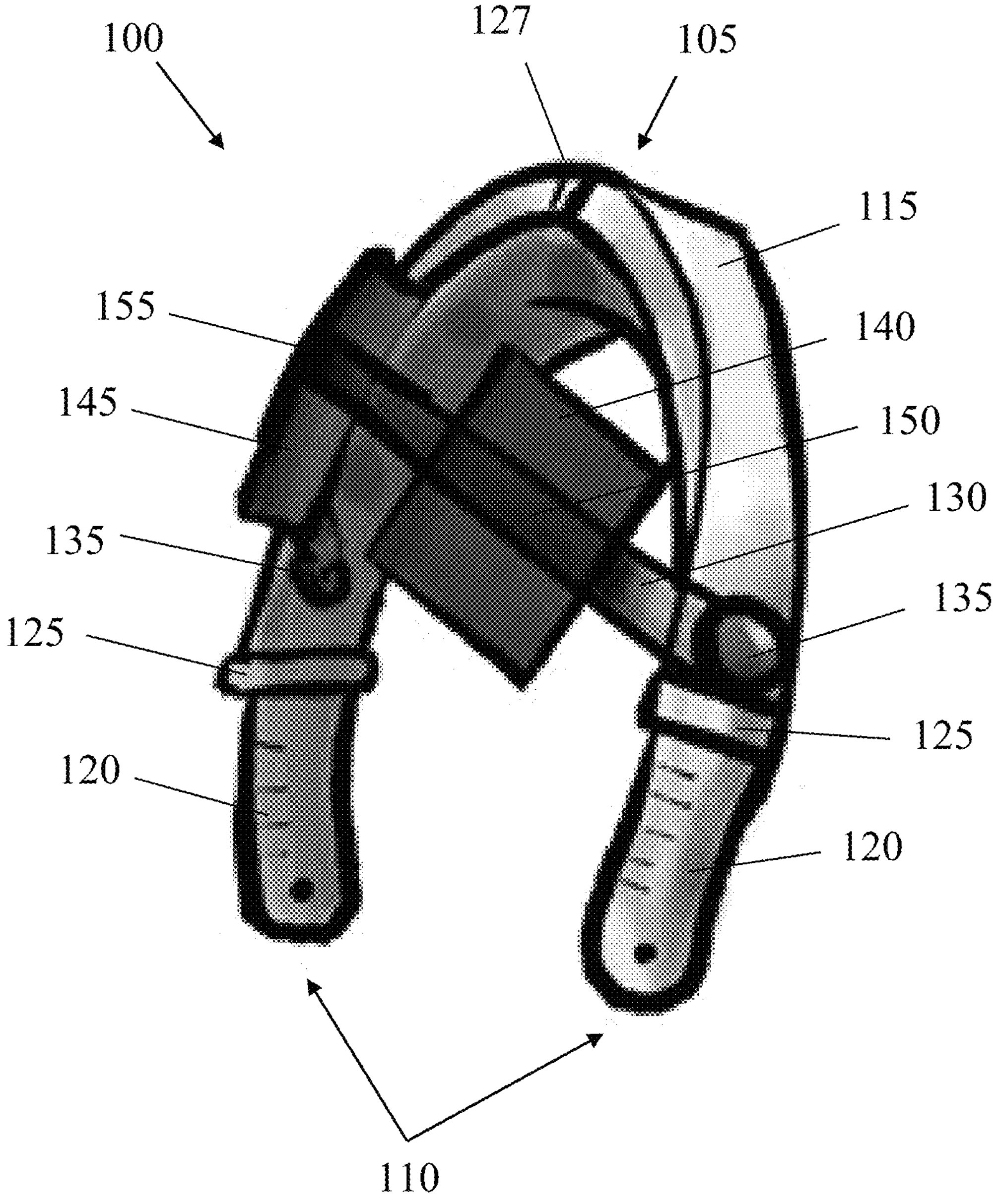
FIG. 1 is an exemplary transcranial direct current stimulation (tDCS) device according to an aspect of the present invention.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The terms "patient," "subject," "individual," "user," and the like are used interchangeably herein, and refer to any animal amenable to the systems, devices, and methods described herein. The patient, subject or individual may be a mammal, and in some instances, a human.

The terms "exercise," "physical activity," and the like are used interchangeably herein, and refer to any increase in energy expenditure through body movement of a subject.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Transcranial Direct Current Stimulation (tDCS) to Enhance a Behavior

The present invention seeks behavioral change through motivation, for example to slow down the rapid increase in sedentary lifestyles by increasing physical activity behavior through motivation, and by targeting specific parts of the brain. Described is an approach under which application of tDCS enhances spontaneous voluntary locomotor activity, physical activity, and exercise, as well as adherence to such behaviors, all of which have considerable health benefits for the general population. This invention proposes that regularly employed transcranial direct current stimulation (tDCS) enhances the physical activity/exercise behavior, as well as adherence to such behavior, in humans. As described herein, in some examples, tDCS is applied directly to the dorsolateral prefrontal cortex (DLPFC) in a way that increases extracellular dopamine in a part of the striatum involved in the reward—motivation pathways. The mechanistic aspects related to the underlying biology of this procedure have been described (Fonteneau et al., Transcranial Direct Current Stimulation Induces Dopamine Release in the Ventral Striatum in Human. Cereb Cortex. 2018; 28(7):2636-46). The proposed invention describes a process in which tDCS is applied alone or in combination with a physical activity and/or stimulus.

In some aspects, the devices, systems, and methods disclosed herein relate to providing noninvasive brain stimulation to enhance a behavior in a subject, for example physical activity behavior. In certain instances, a method of the present disclosure targets and activates the dopaminergic system thereby enhancing physical activity behavior and adherence to physical activity as measured by metrics including, but not limited to, energy expenditure, step count, standing time, physical activity intensity and associated subjective measures for desire to perform physical activity and exercise. In certain embodiments, the invention employs transcranial direct current stimulation (tDCS), a non-invasive brain stimulation method that comprises the application of a low intensity, direct current to areas of the brain facilitating or inhibiting spontaneous neural activity. Aspects of the invention include enhancing motivation for physical activity and/or exercise, increasing the rewarding effects of physical activity and/or exercise, enhancing voluntary, unsupervised physical activity and/or exercise levels, and increasing adherence to physical activity and/or exercise programs.

Although certain exemplary embodiments disclosed herein may discuss performing various tDCS or other neurostimulation methods via a particular device or apparatus, for example the device shown in FIG. 1, it is understood that any particular devices or apparatuses are not essential for the application of the methods disclosed herein. Any suitable neurostimulation device which has the appropriate specifications to perform the methods disclosed herein and apply the neurostimulation discussed in the methods disclosed herein may be used, alone or in combination.

Electrode Positioning Device

Aspects of the present invention relate to a device comprising a headband for fitting over a subject's head with telescoping features for adjusting the size of the device. In some embodiments, the device comprises an electrode band for attaching one or more electrodes and enables transcranial direct current stimulation (tDCS) on the subject. In some embodiments, the one or more electrodes may be attached directly to the headband and/or the electrode band.

Figure 2:
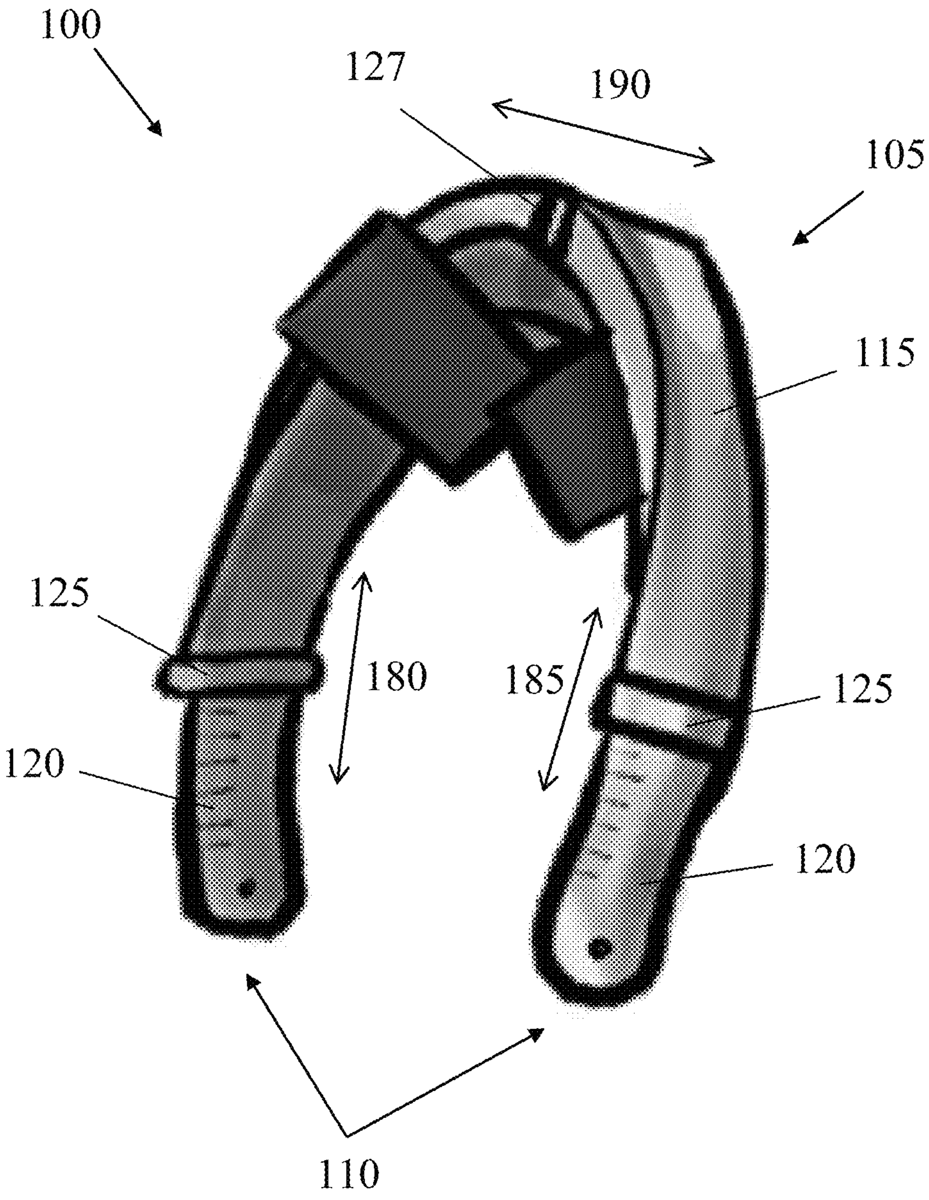
FIG. 2 depicts size-adjustable features of an exemplary tDCS device according to an aspect of the present invention.
Figure 3:
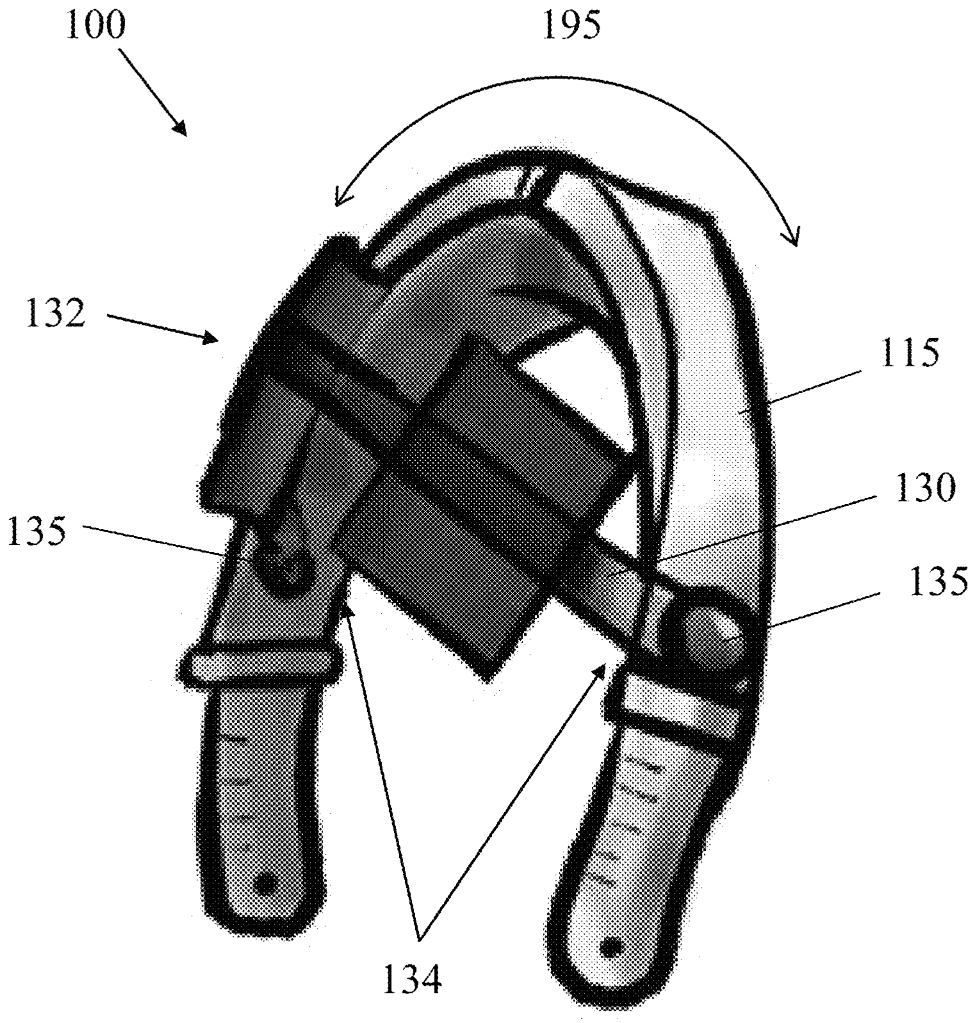
FIG. 3 depicts position-adjustable features of an exemplary tDCS device according to an aspect of the present invention.

Now referring to FIGS. 1 through 3, shown is an exemplary device 100 comprising a headband 115 comprising a curved band having a proximal end 105, distal ends 110, and a length therebetween. In some embodiments, headband 115 comprises a pair of distal tabs 120 slidably attached to distal ends 110. In some embodiments, device 100 further comprises sheaths 125 positioned on distal ends 110 of headband 115, configured to house and slidably receive at least a portion of tabs 120, such that the tabs 120 may telescope in and out of the corresponding sheaths to provide adjustment of the length of distal ends 110 and/or headband 115. In some embodiments, device 100 further comprises an adjustment mechanism 127 positioned laterally on proximal end 105 of headband 115, configured to slidably and telescopically adjust the width of proximal end 105 and/or headband 115. In some embodiments, device 100 further comprises an electrode band 130 comprising a curved band having a proximal end 132, distal ends 134 and a length therebetween. In some embodiments, electrode band 130 is hingedly and rotatably attached to headband 115, wherein distal ends 134 connect via hinges 135 to distal positions on headband 115. In some embodiments, electrode band 130 further comprises electrode mount 150 and electrode mount 155 fixedly and slidably attached to electrode band 130 configured to attach an anode 140 and a cathode 145. In some embodiments, adjustable mount 150 removably and slidably attaches anode 140 to electrode band 130 and allows for adjustment of anode 140 across the length of electrode band. Similarly, in some embodiments, adjustable mount 155 removably and slidably attaches cathode 145 to electrode band 130 and allows for adjustment of cathode 145 across the length of the band.

Although exemplary device 100 depicts anode 140 and cathode 145 in particular positions along the length of electrode band 130, it should be understood that anode 140 and cathode 145 may be removed and reconfigured, replaced and/or interchanged with various forms of electrodes as contemplated herein to fit the desired configuration and method. In some embodiments, anode 140 and/or cathode 145, or any additional electrodes as contemplated herein, may be configured for alternative neurostimulation protocols, or in any positions along electrode band 130, in a range of positions relative to headband 115. It should be understood that electrode band 130 may be rotated relative to headband 115. As electrode band 130 is adjusted in a range of positions relative to headband 115, the headband remains in a fixed position relative to the head of the subject. In some embodiments, this adjustable range allows for arbitrary placement of any contemplated electrodes relative to the head of the subject. In some embodiments, device 100 comprises one or more electrode bands 130 for positioning additional electrodes in contact with the head of the subject. In some embodiments, device 100 further comprises electrodes positioned along the length of headband 115 in contact with the head of the subject. For example, in some embodiments, device 100 comprises a first set of electrodes fixedly and slidably attached to headband 115, and a second set of electrodes fixedly and slidably attached to electrode band 130.

In some embodiments, device 100 is a band having an arcuate shape and overlays a portion of the subject's head on a frontal plane and/or a sagittal plane relative to the subject's head. In some embodiments, device 100, headband 115 and/or electrode band 130 are circular, toroidal, or elliptical in shape and overlay a portion of the subject's head on a transverse plane. Although example shapes are provided, device 100, headband 115 and/or electrode band 130 may comprise any shape that would fit the head of the subject as would be known by one of ordinary level of skill in the art. For example, in certain embodiments, the headband may be in the form of a helmet that covers a portion of the subject's head. In another example, the headband may comprise a fabric hat or cap that covers a portion of the subject's head.

In some embodiments, headband 115 is configured to fit the head of a subject on the frontal plane and position electrode band 130 in proximity to various points on the subject's head. In some embodiments, electrode band 130 extends around at least a portion of the subject's head. In some embodiments, electrode band 130 may be configured to a range of positions over the head of the subject. In some embodiments, the range of positions may extend between the nasion (see FIG. 4), and further rotating to the back of the head to a position over the inion (see FIG. 4). In some embodiments, electrode band 130 may be configured to lock at one or more specific positions and/or angles of rotation with respect to headband 115, allowing for targeting of any arbitrary electrode placement positions, including but not limited to all ECG electrode placement positions (see FIG. 4). As a result, device 100 as disclosed may be adapted and/or configured to any neurostimulation or tDCS protocol.

Telescoping Features/Adjustment

Aspects of the present invention relate to telescoping features and adjustability of device 100. In some embodiments, device 100 comprises telescopically inter-engaged components to allow the subject and/or caregiver to adjust the size of the device to the subject's head and/or an appropriate fitment. Aspects of device 100 may extend or retract to allow the device to securely fit heads of various shapes and sizes. Now referring to FIG. 2, shown are the directions that components of device 100 may telescopically extend or retract on. In some embodiments, device 100 may telescope in lateral and vertical directions to adjust to the size of the device to the subject's head. As shown, device 100 may be adjusted on axis 180 and axis 185 to extend or retract distal tabs 120, and adjust the length of the device on the sagittal plane with respect to the subject's head. In some embodiments, distal tabs 120 telescope in and out of sheaths 125 along axes 180, 185 to adjust the vertical length of the device. In some embodiments, device 100 comprises lateral telescoping features to adjust the width of the device on the frontal plane with respect to the subject's head. As shown, adjustment mechanism 127 positioned on proximal end 105 of headband 115 may extend or retract along axis 190 to adjust the width of the headband. In some embodiments, the telescoping features along axes 180, 185, 190 of device 100 comprise ratcheting mechanisms with discrete locking positions. In some embodiments, adjustment mechanism 127 comprises a tab and two laterally opposed sheaths, the sheaths configured to receive a portion of the tab and adjust along axis 190. In some embodiments, the distal telescoping features of device 100 comprise brake mechanisms to lock the telescoping positions of tabs 120 along axes 180 and 185. In some embodiments, adjustment mechanism 127 comprises one or more brake mechanisms to lock the telescoping positions of headband 115 along axis 190.

In some embodiments, headband 115 and/or electrode band 130 comprise a hollow inner channel or lumen. In some embodiments, headband 115 and/or electrode band 130 comprise one or more apertures on the surface to access the hollow inner channel or lumen. In some embodiments, headband 115 and/or electrode band 130 comprise one or more internal reinforcing components. In some embodiments, the internal reinforcing component of headband 115 and/or headband 130 may comprise an alloy metal, a carbon fiber or an elastic material. In some embodiments, the internal reinforcing component of headband 115 and/or electrode band 130 is in the form of a honeycomb structure. In some embodiments, headband 115 may comprise a hollow inner channel in fluid communication with a hollow inner channel of electrode band 130. In some embodiments, headband 115 and/or electrode band 130 are electrically connected and/or comprise electrical wires. In some embodiments, the electrical wires reside in the hollow inner channel of headband 115 and/or electrode band 130. In some embodiments, electrical wires enter the hollow inner channel of headband 115 from the one or more apertures on the surface of headband 115. In some embodiments, electrical wires enter the hollow channel of headband 115 from the one or more apertures and connect to the hollow interior channel of electrode band 130 through an aperture passing through hinge 135.

In some embodiments, electrode band 130 is mounted to headband 115 in locations proximal to distal ends 110. In some embodiments, electrode band 130 fixedly, hingedly rotatably, and/or removably connects to headband 115 in one or more locations. In some embodiments, electrode band 130 hingedly connects to headband 115 with hinges 135 that rotate and/or pivot on one or more planes. In some embodiments, hinge 135 comprises an opening passing through the hinge that fluidly connects the lumens of electrode band 130 and headband 115. In some embodiments, electrode band 130 may pivot on one or more axis. In some embodiments, electrode band 130 comprises two ends, with each end hingedly and rotatably attached to headband 115. In some embodiments, electrode band 130 may be adjusted along a semicircle path on the sagittal plane with respect to the subject's head.

Now referring to FIG. 3, shown is an exemplary device 100 with various adjustable features of electrode band 130. In some embodiments, electrode band 130 may be adjusted along axis 195 such that electrode band 130 is positioned in proximity to various points on the subject's head. In some embodiments, electrode band 130 may be adjusted along axis 195 on the sagittal plane of the subject's head in positions ranging from the nasion to the inion. In some embodiments, electrode band 130 adjusts to one or more pre-determined positions in an arcuate path along the sagittal plane between the nasion and inion of the subject's head.

Figure 4:
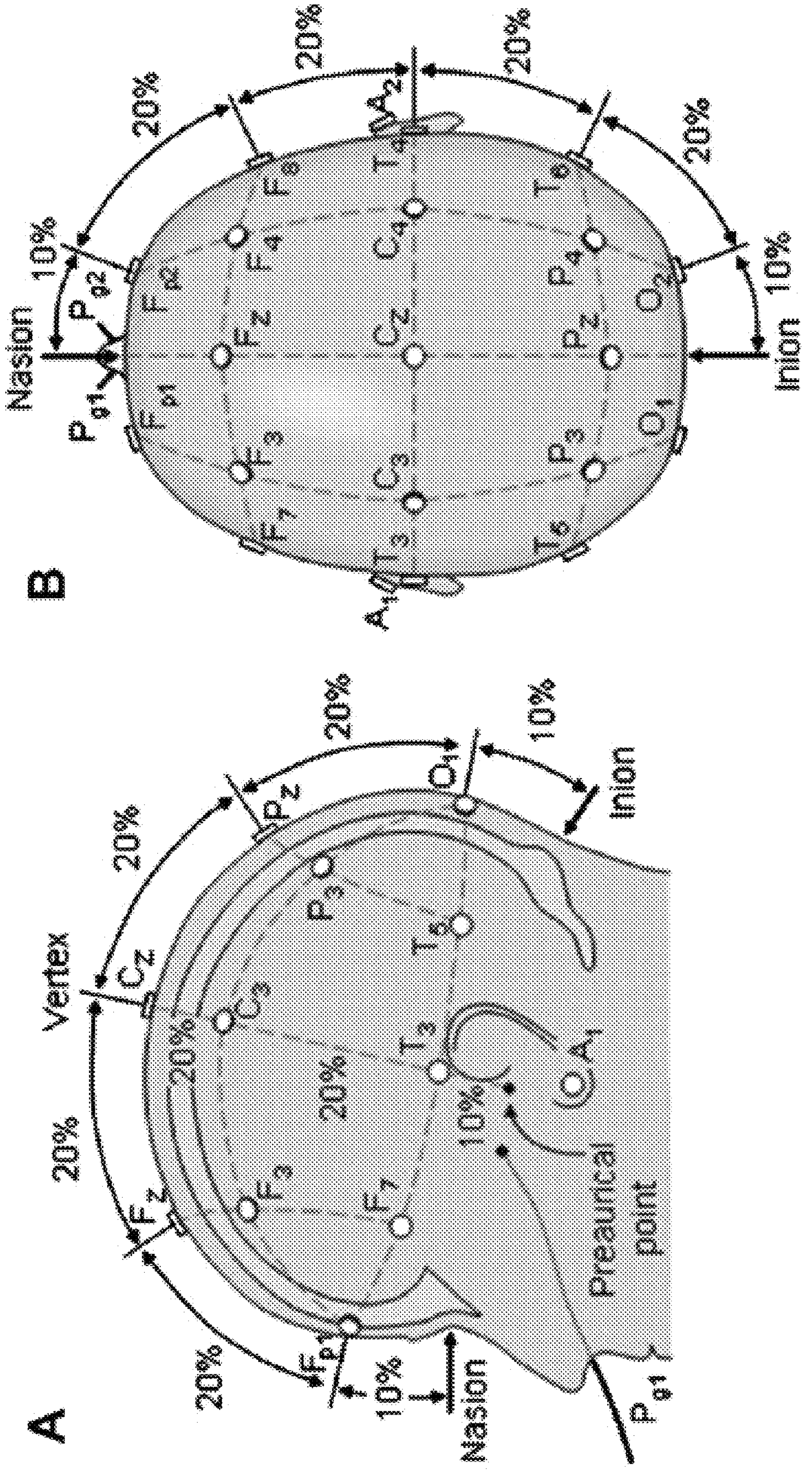
FIG. 4 depicts a side view (left) and top down view (right) of the international 10-20 system for scalp electrode placement.

Now referring to FIG. 4, shown are exemplary locations on a subject's head that may be used for electrode placement for neurostimulation. In some embodiments, electrode band 130 is adjustable to a range of positions in proximity to the locations described in the international 10-22 system for critical scalp electrode location points. In some embodiments, electrode band 130 comprises one or more sensors for determining the position of electrode band with respect to headband 115, the subject's head, and/or the ground. In some embodiments, electrode band 130 comprises one or more sensors to determine if device 100 is placed the head of the subject. In some embodiments, electrode band 130 comprises one or more sensors to determine if the electrodes (i.e. anode 140 and cathode 145) are in contact with the head of the subject. In some embodiments, electrode mounts 150 and 155 comprise magnets for determining the positions of the electrodes along the frontal plane of the subject.

Again referring to FIG. 1, the present invention provides a device that positions electrodes in contact with the head of a subject. In some embodiments, electrode band 130 may attach one or more electrodes. In some embodiments, electrode band 130 fixedly attaches electrodes, for example anode 140 and cathode 145. In some embodiments, electrode band 130 fixedly, hingedly and slidably attaches one or more electrodes with adjustable mounting points. In some embodiments, device 100 comprises a first and second electrode. For example, electrode band 130 may connect two electrodes, the first electrode being anode 140 and the second being cathode 145. In some embodiments, the electrodes are configured to fixedly and removably attach to one or more electrode mounting points (i.e. electrode mounts 150 and 155). In some embodiments, electrode band 130 comprises one or more channels in the band for slidable adjustment of one or more electrodes to various positions across the length of the band. In some embodiments, electrode band 130 comprises one or more electrode channels to affix electrode mount 150 and electrode mount 155 along an arcuate path. In some embodiments, the electrodes can slide along the length of electrode band 130 for adjustment to various positions. In some embodiments, the electrode channel comprises one or more conductive elements for providing electrical current to the one or more electrodes. In some embodiments, electrode band 130 comprises one or more sensors for calculating the positions of the one or more electrodes along the length of the electrode channel and/or electrode band 130.

Aspects of the present invention relate to one or more electrodes placed in contact with the head of the subject to administer neurostimulation, including but not limited to neurostimulation with low intensity direct current. In some embodiments, device 100 comprises headband 115 connected to electrode band 130 which hosts electrodes anode 140 and cathode 145, wherein the electrodes make contact with a subject's head in order to perform transcranial direct current stimulation (tDCS). In some embodiments, one or more electrodes transmit electrical current to specific locations on the subject's head. In alternative embodiments, other neurostimulation methods may be administered using the devices and systems disclosed herein, including but not limited to tACS (transcranial alternating current stimulation).

Figure 5:
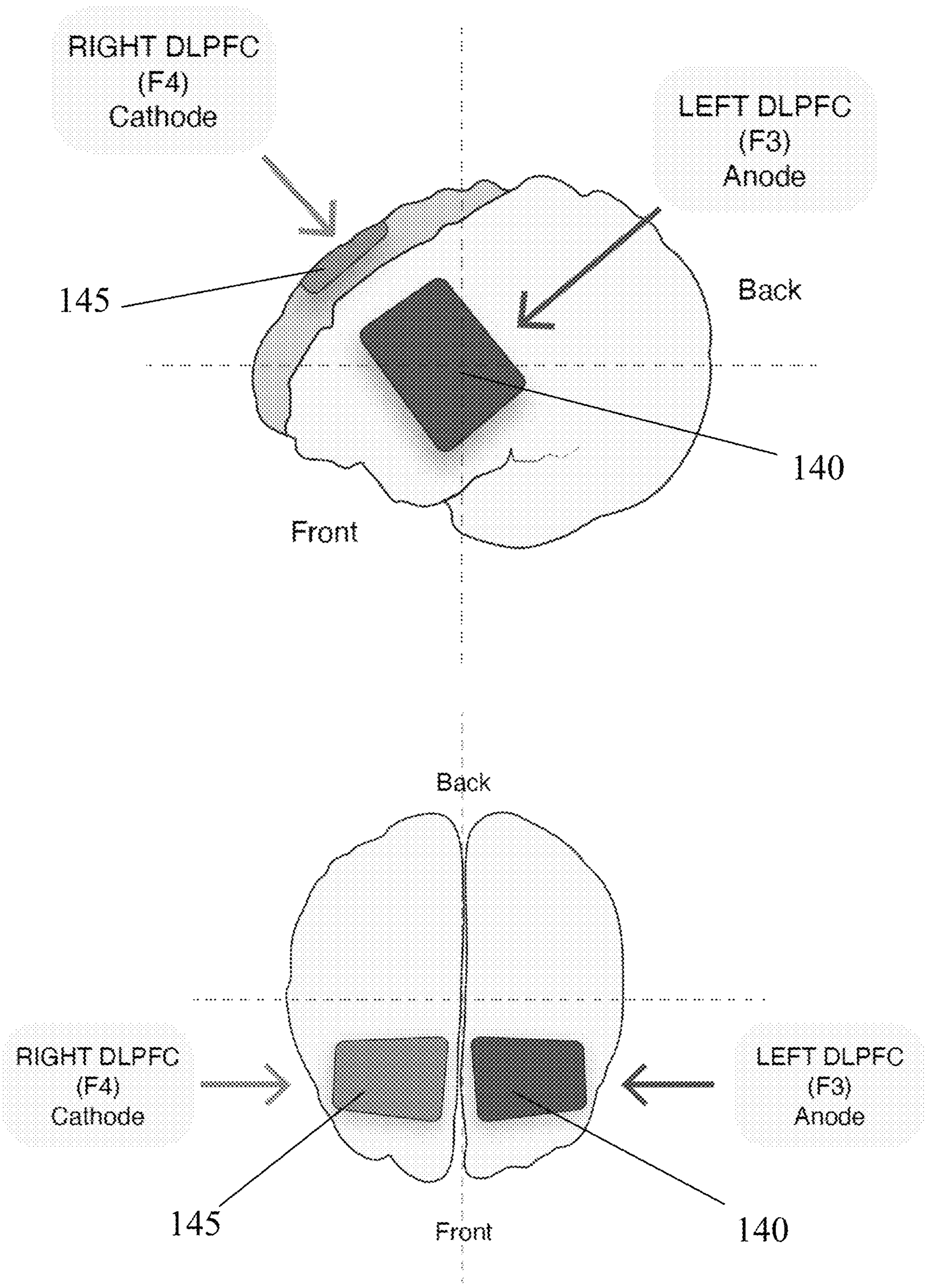
FIG. 5 depicts a perspective view (top) and top view (bottom) of an exemplary electrode placement on a scalp with the anode at the F3 location stimulating the left dorsolateral prefrontal cortex (DLPFC) and the cathode at the F4 location stimulating the right dorsolateral prefrontal cortex (DLPFC).

Referring now to FIG. 5, exemplary positions for anode 140 and cathode 145 are shown. In some embodiments, anode 140 is positioned at the F3 location stimulating the left dorsolateral prefrontal cortex (DLPFC) and cathode 145 at the F4 location stimulating the right dorsolateral prefrontal cortex (DLPFC).

Aspects of the present invention relate to electrode sizes for anode 140 and cathode 145. In some embodiments. the electrode size for anode 140 and cathode 145 may range in size as measured by area. In some embodiments, the electrodes may be about 2 $cm^2$, 4 $cm^2$, 6 $cm^2$, 8 $cm^2$, 10 $cm^2$, 12 $cm^2$, 14 $cm^2$, 16 $cm^2$, 18 $cm^2$, 20 $cm^2$, 22 $cm^2$, 24 $cm^2$, 26 $cm^2$, 28 $cm^2$, 30 $cm^2$, 32 $cm^2$, 34 $cm^2$, 36 $cm^2$, 38 $cm^2$, 40 $cm^2$, 42 $cm^2$, 44 $cm^2$, 46 $cm^2$, 48 $cm^2$ or about 50 $cm^2$ or individual values or ranges therebetween. For example, in some embodiments the electrodes may be about 35 $cm^2$.

Aspects of the present invention relate to electrode types for device 100. In some embodiments, the electrodes of device 100 are any of pad electrodes, sponge electrodes, foam electrodes, rubber electrodes, and any combination thereof. In some embodiments, a sponge covers an entire electrode, and may be wetted with a liquid, for example a conductive liquid, to aid in current transmission. In some embodiments, any electrode as contemplated herein may be used without any sponge or pad, for example using a current-conductive gel or cream at the junction between the electrode and the head of the subject. Although some examples are provided, the electrodes may comprise any material, shape or size as would be applied for neurostimulation by someone with ordinary level of skill in the art.

In some embodiments, device 100 comprises one or more sensors to determine the position of electrode band 130, anode 140 and/or cathode 145 with respect to the subject's head. In some embodiments, device 100 comprises one or more Inertial Measurement Units (IMUs) to calculate the spatial orientation of device 100. In some embodiments, device 100 comprises one or more IMUs to calculate the position of electrode band 130 with respect to headband 115. In some embodiments, device 100 may comprise one or more IMUs in contact with headband 115 and/or electrode band 130 in order to calculate the orientations of the device 100 in space and/or relative to the ground. In some embodiments, device 100 comprises one or more rotary encoders to determine the position of electrode band 130 with respect to headband 115 and/or device 100. In some embodiments, device 100 comprises one or more sensors to determine the positions of electrodes anode 140 and cathode 145. In some embodiments, electrode band 130 comprises limit switches and/or linear switches to determine the positions of the electrodes. In some embodiments, device 100 may comprise hall-effect sensors to determine the position of the electrodes using magnets mounted in the electrode mounts. In some embodiments, device 100 comprises sensors and/or switches to determine if the device is being worn by the subject (e.g. a proximity sensor).

In some embodiments, device 100 comprises a combination of plastic and/or metal materials. In some embodiments, device 100 comprises a combination of plastic, flexible, elastic and/or metal materials. In some embodiments, device 100 comprises a fabric, plastic, elastic and/or metal material. In some embodiments, device 100 comprises 3D printed materials. In some embodiments, device 100 comprises a combination of conductive and non-conductive materials. In some embodiments, device 100 comprises polymers and/or other materials known in the art. Although example materials are provided, device 100 may comprise additional materials as would be known by someone with ordinary level of skill in the art.

Neurostimulator System

Figure 6:
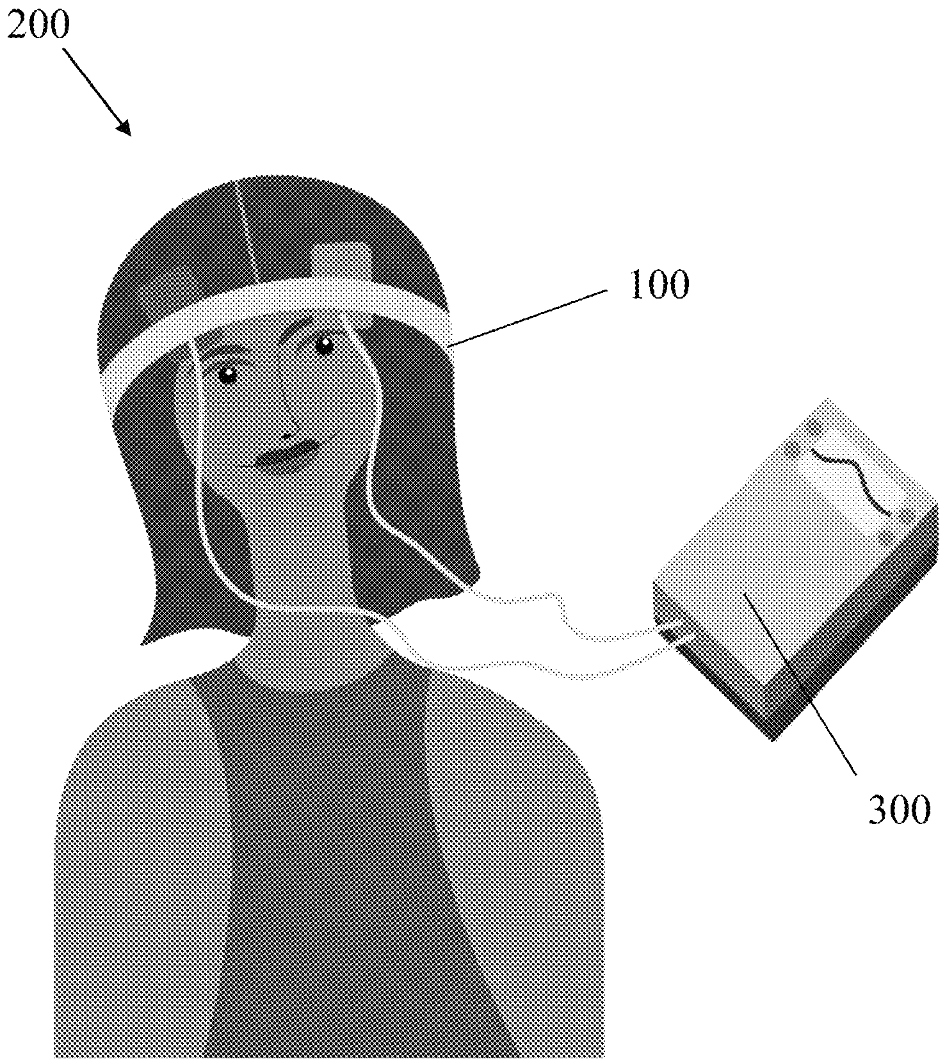
FIG. 6 depicts a conventional tDCS stimulator connected to a tDCS device mounted on the head of a subject.
Figure 7:
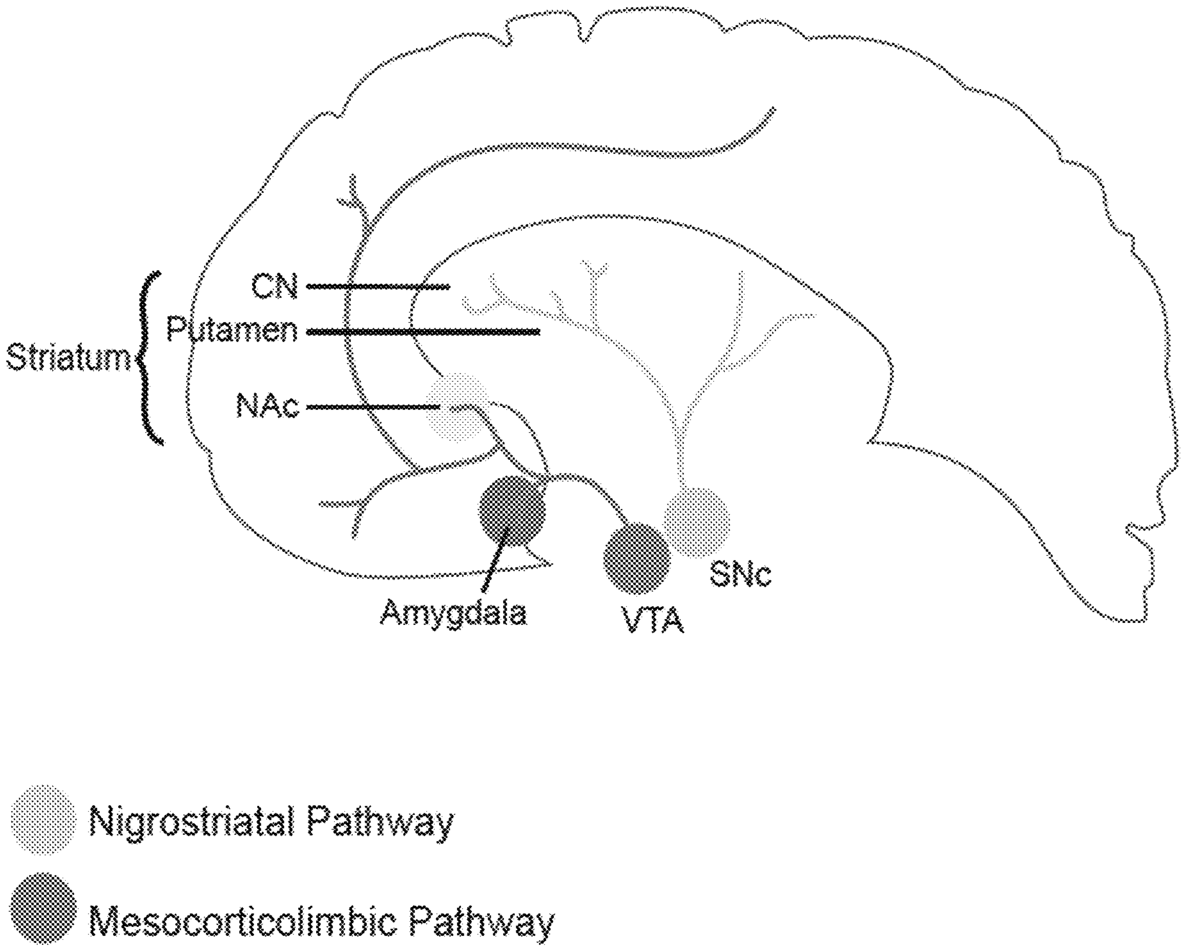
FIG. 7 is a diagram depicting the dopaminergic pathways of the human brain including the nigrostriatal pathway and mesocorticolimbic pathway.
Figure 8:
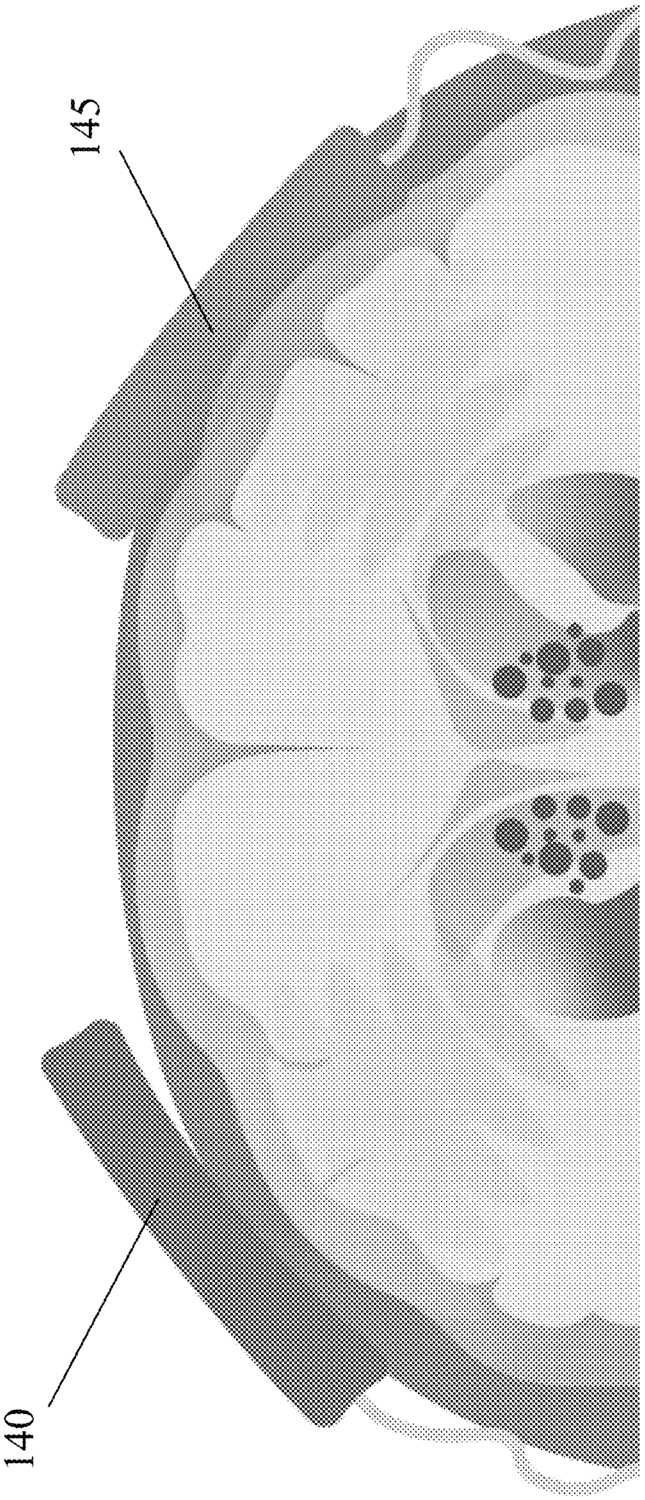
FIG. 8 is a diagram depicting an exemplary electrode positioning for neurostimulation of the dopaminergic pathways of the human brain using the electrodes of a conventional tDCS device.

Aspects of the present invention relate to a neurostimulator system for applying a neurostimulation to a subject, for example a low intensity direct current, by one or more electrodes for a given period of time. In some embodiments, the present invention provides a system 200 comprising device 100 and a neurostimulator device 300. For example, in some embodiments, the electrodes of device 100 are connected to neurostimulator device 300, wherein device 300 provides power, control and/or electrical signals to device 100. Now referring to FIG. 6, shown is an exemplary system 200 comprising any device 100 of the present invention having one or more electrodes positioned on the head of a subject, connected to a neurostimulator device 300. In some embodiments, device 100 is electrically connected to device 300 via electrical leads, wires, and the like. In some embodiments, device 100 comprises a power source (e.g. a battery) and connects to device 300 wirelessly to control the neurostimulation. Although FIG. 6 depicts system 200 comprising device 100 of the present invention, it should be understood that any neurostimulation apparatus having one or more electrodes may be used in the place of device 100.

As contemplated herein, any system, device, or method of the present invention may be used for any type of neuromodulation or neurostimulation, for example transcranial direct current stimulation (tDCS). It should be understood that the devices and systems disclosed herein may be used with any other form of neuromodulation or neurostimulation, including but not limited to transcranial alternating current stimulation (tACS).

Figure 13:
FIG. 13 depicts a subject in a study undergoing tDCS with electrodes with a conventional tDCS device placed on the head.

The methods disclosed herein may be applied with any neurostimulator device, for example a home-based device, commercially available device, or a research grade device. A neurostimulator device for use with the methods disclosed herein may comprise device 300 and is connected to electrodes to be placed on a subject's head. For example, device 300 may be connected to device 100, as described elsewhere herein, or any conventional neurostimulator apparatus. In some embodiments, system 200 and/or device 300 comprises commercial-off-the-shelf components. In some embodiments, device 300 is a DC-Stimulator Plus (shown in FIG. 13). In some embodiments, device 100, system 200 and/or device 300 comprises a computing device 900 as described herein. In some embodiments, device 300 electrically and/or wirelessly connects to device 100, or any neurostimulation apparatus, and provides an electrical current for a pre-determined period of time according to the methods disclosed herein. In some embodiments, device 100, system 200, device 300 and/or computer 900 has pre-programmed neurostimulation durations and intensities. In some embodiments, device 100, system 200, device 300 and/or computer 900 has subject programmable neurostimulation durations and intensities.

Computing Device

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C #, Objective-C, Java, JavaScript, MATLAB, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Figure 9:
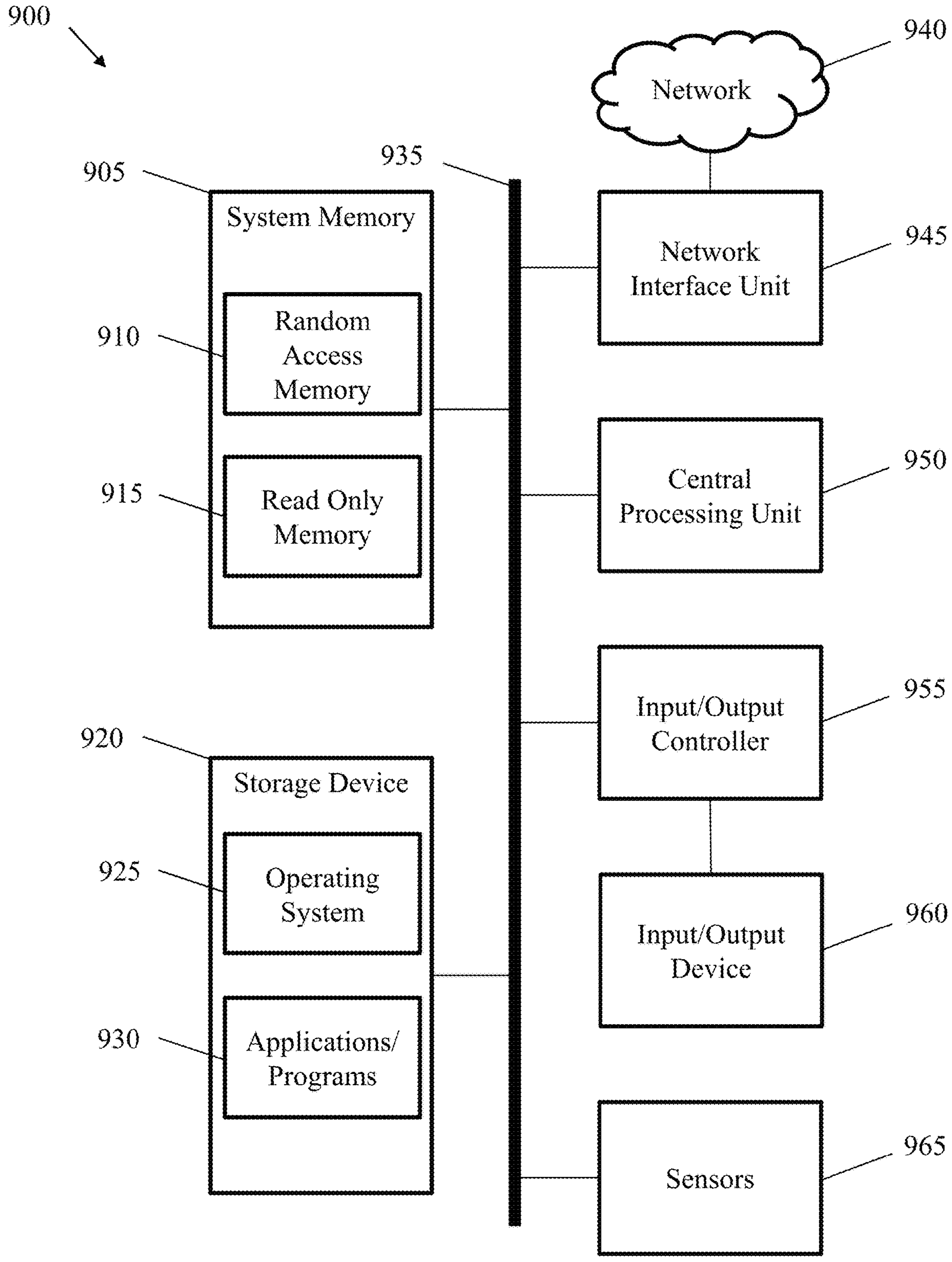
FIG. 9 is an exemplary diagram of a computing device according to an aspect of the present invention.

FIG. 9 and the following discussion are intended to provide a brief, general description of a suitable computing environment in which the invention may be implemented. While the invention is described above in the general context of program modules that execute in conjunction with an application program that runs on an operating system on a computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

FIG. 9 depicts an illustrative computer architecture for a computer 900 for practicing the various embodiments of the invention. The computer architecture shown in FIG. 9 illustrates a conventional personal computer, including a central processing unit 950 ("CPU"), a system memory 905, including a random access memory 910 ("RAM") and a read-only memory ("ROM") 915, and a system bus 935 that couples the system memory 905 to the CPU 950. A basic input/ output system containing the basic routines that help to transfer information between elements within the computer, such as during startup, is stored in the ROM 915. The computer 900 further includes a storage device 920 for storing an operating system 925, application/program 930, and data.

The storage device 920 is connected to the CPU 950 through a storage controller (not shown) connected to the bus 935. The storage device 920 and its associated computer-readable media provide non-volatile storage for the computer 900. Although the description of computer-readable media contained herein refers to a storage device, such as a hard disk or CD-ROM drive, it should be appreciated by those skilled in the art that computer-readable media can be any available media that can be accessed by the computer 900.

By way of example, and not to be limiting, computer-readable media may comprise computer storage media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

According to various embodiments of the invention, the computer 900 may operate in a networked environment using logical connections to remote computers through a network 940, such as TCP/IP network such as the Internet or an intranet. The computer 900 may connect to the network 940 through a network interface unit 945 connected to the bus 935. It should be appreciated that the network interface unit 945 may also be utilized to connect to other types of networks and remote computer systems.

The computer 900 may also include an input/output controller 955 for receiving and processing input from a number of input/output devices 960, including a keyboard, a mouse, a touchscreen, a camera, a microphone, a controller, a joystick, or other type of input device. Similarly, the input/output controller 955 may provide output to a display screen, a printer, a speaker, or other type of output device. The computer 900 can connect to the input/output device 960 via a wired connection including, but not limited to, fiber optic, Ethernet, or copper wire or wireless means including, but not limited to, Wi-Fi, Bluetooth, Near-Field Communication (NFC), infrared, or other suitable wired or wireless connections.

As mentioned briefly above, a number of program modules and data files may be stored in the storage device 920 and/or RAM 910 of the computer 900, including an operating system 925 suitable for controlling the operation of a networked computer. The storage device 920 and RAM 910 may also store one or more applications/programs 930. In particular, the storage device 920 and RAM 910 may store an application/program 930 for providing a variety of functionalities to a subject. For instance, the application/program 930 may comprise many types of programs such as a word processing application, a spreadsheet application, a desktop publishing application, a database application, a gaming application, internet browsing application, electronic mail application, messaging application, and the like. According to an embodiment of the present invention, the application/program 930 comprises a multiple functionality software application for providing word processing functionality, slide presentation functionality, spreadsheet functionality, database functionality and the like.

The computer 900 in some embodiments can include a variety of sensors 965 for monitoring the environment surrounding and the environment internal to the computer 900. These sensors 965 can include a Global Positioning System (GPS) sensor, a photosensitive sensor, a gyroscope, a magnetometer, thermometer, a proximity sensor, an accelerometer, a microphone, biometric sensor, barometer, humidity sensor, radiation sensor, or any other suitable sensor.

Methods of Use

Aspects of the present invention relate to methods of administering neurostimulation (e.g. tDCS) to a subject. In some embodiments, the methods further comprise providing a stimulus before, after or during the administration of neurostimulation. In some embodiments, the stimulus comprises an audio and/or visual alert to perform physical activity or exercise. In some embodiments, the stimulus is presented to the subject, and is a representation or depiction of a physical activity, including but not limited to an aerobic or resistance exercise. In some embodiments, the stimulus presented to the subject is a depiction of other people performing physical activity. In some embodiments, the stimulus comprises a picture, shape, color or sound. Although exemplary stimuli are provided, the stimulus may comprise any suitable stimulus as would be known by someone with an ordinary level of skill in the art. In some embodiments, the stimulus is in the form of an audio or visual format ranging between 2 and 6 minutes. In some embodiments, the stimulus involves observing exercise on a screen monitor (e.g., a TV, computer, tablet, or phone) or audio output (e.g., radio, and other devices with speakers). In some embodiments, the stimulus may be a verbal command. In some embodiments, the stimulus may be a written document or schedule. In some embodiments, the stimulus is in the form of an audible notification. In some embodiments, the stimulus is in the form of a visual notification. In some embodiments, the stimulus may be presented to the subject with device 100, system 200, device 300 and/or computing device 900. In some embodiments, the stimulus may be sent from device 100, system 200, device 300 and/or computing device 900 to the subject's handheld device (e.g. a cellphone or tablet). In some embodiments, the stimulus is sent to the handheld device as a push notification, a text message, a phone-call, an email and/or other forms of digital communication. In some embodiments, multiple stimuli as disclosed may be delivered simultaneously or sequentially, before, during, or after any disclosed treatment.

Although certain embodiments disclosed herein may be presented in the context of using neuromodulation or neurostimulation to encourage or discourage a particular activity or behavior (for example, tDCS in conjunction with physical-activity-related stimuli in order to encourage physical activity in a subject), it is understood that the devices and methods disclosed herein may be applied interchangeably to any behavior modification treatment, including but not limited to treatment for alleviating eating disorders, smoking cessation, anger management, treatments to mitigate depression, treatments to reduce or eliminate drug use, treatments to reduce or alleviate anxiety, to overcome phobias, to increase comfort in public speaking or other social interactions, to improve study or working habits, or any other behavior modification process.

For example a method of encouraging or discouraging a behavior as disclosed herein may comprise positioning one or more electrodes on a subject, providing a stimulus to the subject related to the behavior to be encouraged, and providing a neuromodulation or neurostimulation to the subject via the one or more electrodes in conjunction with the stimulus. In some embodiments, the stimulus is provided before, during, or after the neuromodulation or neurostimulation. As a result, the neural response to the neuromodulation or neurostimulation via the electrodes induces a desired change in behavior.

Methods of Enhancing Physical Activity Behavior Using Neuromodulation

Aspects of the present invention relate to a method of enhancing the physical activity of a subject via neuromodulation or neurostimulation. In some embodiment, the method comprises providing a tDCS device for neurostimulation. In some embodiments, the method comprises providing a tDCS device and one or more stimulus. In some embodiments, the method comprises providing a neurostimulation before, during or after the one or more stimulus. In some embodiments, the method comprises providing a tDCS device, administering a neurostimulation, and encouraging physical activity. In some embodiments, the neurostimulation is administered before, during or after the physical activity. In some embodiments, the method comprises administering a neurostimulation, providing one or more stimulus and encouraging a physical activity. In some embodiments, the neurostimulation, one or more stimulus and physical activity may occur in any order and with any frequency. In some embodiments, the physical activity or exercise (including visual or audio stimulus) is applied concurrent with the tDCS stimulation, prior, or after the tDCS stimulation. In some embodiments, the stimulus may comprise aerobic or resistance exercise, and/or visual or audio representation of exercise.

Aspects of the present invention provide a method for neurostimulation. In some embodiments, the method for neurostimulation comprises the steps of providing any device 100 of the present invention, or providing any neurostimulator device, or providing any neurostimulator device 300, or providing any system 200 of the present invention, connecting device 100 to device 300, and programming a neurostimulation intensity and duration. In some embodiments, the method further comprises providing one or more stimulus, and/or encouraging one or more physical activities. In some embodiments, the method for neurostimulation further comprises the step of providing an electrical current for about 1 min, 2 min, 4 min, 6 min, 8 min, min, 12 min, 14 min, 16 min, 18 min, 20 min, 22 min, 24 min, 26 min, 28 min, 30 min, 32 min, 34 min, 36 min, 38 min, 40 min, 42 min, 44 min or about 45 minutes or individual values or ranges therebetween. For example, in some embodiments the electrical current is administered for 20 minutes. In some embodiments, the method further comprises providing an electrical current of about 1 mA, 1.25 mA, 1.5 mA, 1.75 mA, 2 mA, 2.25 mA, 2.5 mA, 2.75 mA, 3.0 mA, 3.25 mA, 3.5 mA, 3.75 mA, 4.0 mA, 4.25 mA, 4.5 mA, 4.75 mA, 5.0 mA, 5.25 mA, 5.5 mA, mA or about 6.0 mA or individual ranges or values therebetween. For example, in some embodiments the method includes providing an electrical current of 2 mA.

Aspects of the present invention provide a method of treatment that comprises tDCS, one or more stimulus and/or physical activity in any order with any frequency. In some embodiments, the method involves treating a subject one or more times. In some embodiments, the method treating a subject more than once per day, once a day, more than once a week, once a week, once a month, and/or any combination thereof. In some embodiments, the method involves providing a treatment schedule as would be known by someone having an ordinary level of skill in the art. For example, the treatment may consist of 20 mins of tDCS neurostimulation, followed by brisk walking for 30 mins, 3 times a week.

A method to enhance the physical activity of a subject via the administration of tDCS using a device and a stimuli is described herein. In some embodiments, the method comprises the step of vetting a subject to determine the presence of conditions including, but not limited to, heart conditions, abnormal blood pressures, pregnancy, a disposition to motion sickness or dizziness, bleeding, infection, blood clots, muscle spasms, neuropathy and medical sensitivity to electricity. If confirmed the subject is not at risk for neurostimulation therapy, the method further comprises the step of preparing the head of the subject by removing any non-permanent materials including, but not limited to, headphones, hearing aids, hats, scarves, prosthesis, hair gels and other hair products.

In some embodiment, any disclosed method further comprises using a tDCS system, including but not limited to device 100. In some embodiments, the method comprises placing device 100 on the head of the subject. In some embodiments, the method further comprises adjusting headband 115 and/or electrode band 130 to correctly fit the subject's head. In some embodiments, the method comprises adjusting the width of headband 115 on proximal end 105 of device 100 by pulling outwards or pushing inwards on headband 115 on axis 190. In some embodiments, the method involves adjusting the length of headband 115 on distal ends 110 of device 100 by pulling downwards or pushing upwards on tabs 120 along axes 180 and 185. In some embodiments, the method comprises the subject adjusting device 100 to fit their head and/or the subject administering any disclosed treatment method.

In some embodiments, any disclosed method comprises positioning the electrodes in unique positions in contact with the subject's head. In some embodiments, electrode band 130, anode 140 and cathode 145 are positioned in proximity to the location on the subject's head that is targeted in the neurostimulation. In some embodiments, the method involves positioning anode 140 in contact with the F3 position of the DLPFC, and cathode 145 in the F4 position of the DLPFC (as shown in FIG. 5).

In some embodiments, any disclosed method involves neurostimulation, using for example device 100 as described, performed for a range of about 2-45 minutes. For example, the neurostimulation is performed for about 20 minutes. In some embodiments, an electrical current in the range of 1-6 mA is administered to the subject through the electrodes for the duration of the treatment. For example, in some embodiments, the electrical current is administered with 2 mA of current for the duration of the treatment. In some embodiments, the electrical current is dynamic throughout the duration of the treatment period. For example, the current may be ramped up and down throughout the duration of the treatment. In some embodiments, the current may comprise an alternating current (for example for use in tACS). In some embodiments, the subject controls the duration and/or strength of the neurostimulation. In some embodiments, the duration and/or strength of the neurostimulation is controlled by an individual overseeing the treatment, such as a health care provider.

In some embodiments, any disclosed method also comprises administering one or more stimulus to encourage or prompt the subject to begin physical activity. In some embodiments, the method comprises presenting the stimuli to the subject, before, during and/or after the physical activity. In some embodiments, the method comprises presenting a subject with depictions of others performing physical activities.

In some embodiments, any disclosed methods comprise having the subject perform exercise or physical activity. In some embodiments, exercise/physical activity is performed in the form of: 1. aerobic (including walking, running, cycling, elliptical, swimming, etc, performed at an intensity corresponding between 10% and 100% of heart rate max), 2. resistance (including resistance ranging between 5% and 100% of maximal force production, repetitions ranging between 2 and 100, and heart rate ranging between 10% and 100% of heart rate max), and for a period between 2 and 60 minutes.

In some embodiments, any disclosed method also comprises tracking the physical activity of the subject. In some embodiments, the method comprises providing a physical activity tracker and monitoring the movement of the subject before, during and after the neurostimulation. In some embodiments, the method further comprises tracking of physical activity before, during and after the physical activity stimulus.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the system and method of the present invention. The following working examples therefore, specifically point out the exemplary embodiments of the present invention, and are not to be construed as limiting in any way the remainder of the disclosure.

Figure 10:
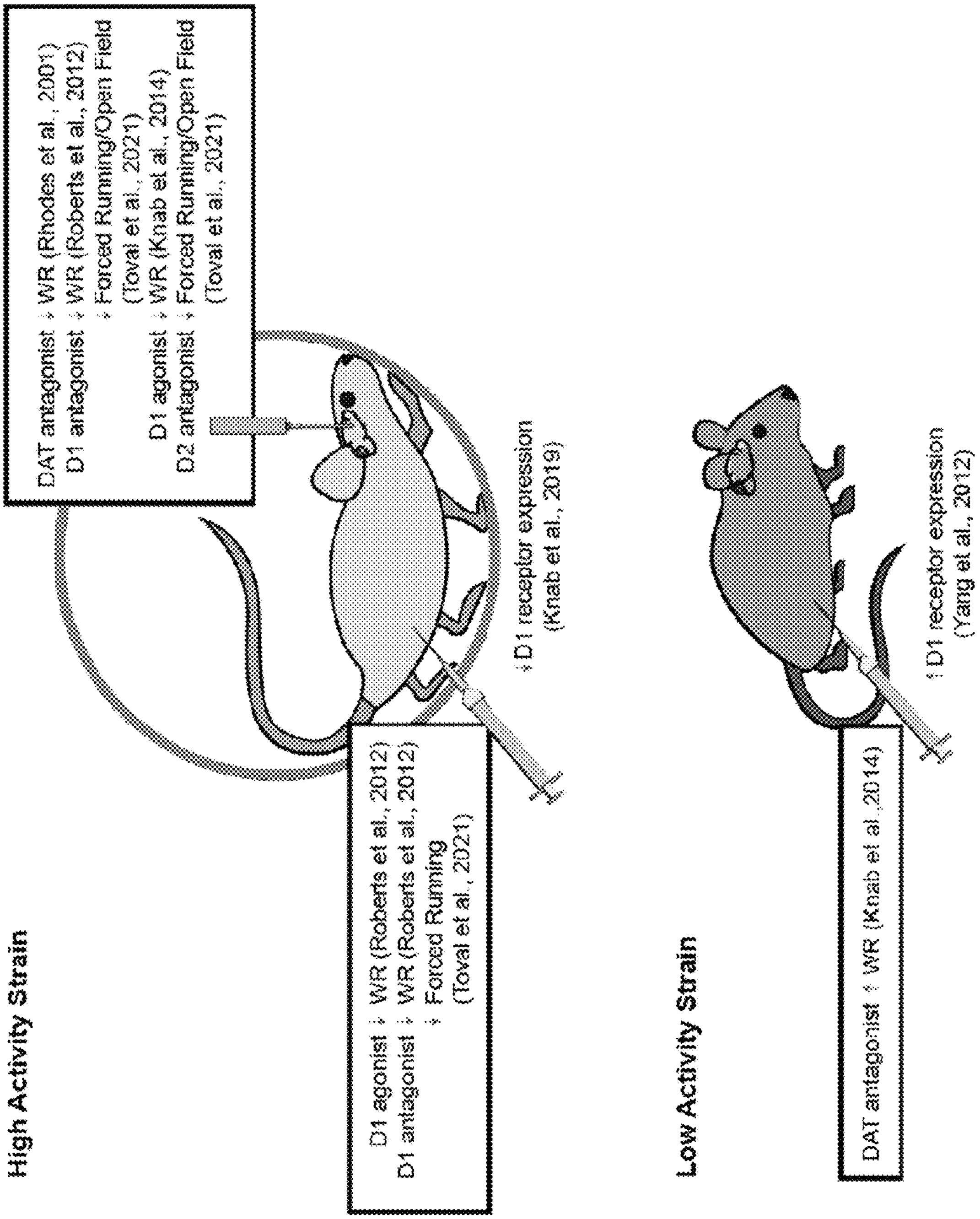
FIG. 10 is a graphic summary of background research on the role of dopaminergic systems in modulating physical activity behavior in a rodent.
Figure 11:
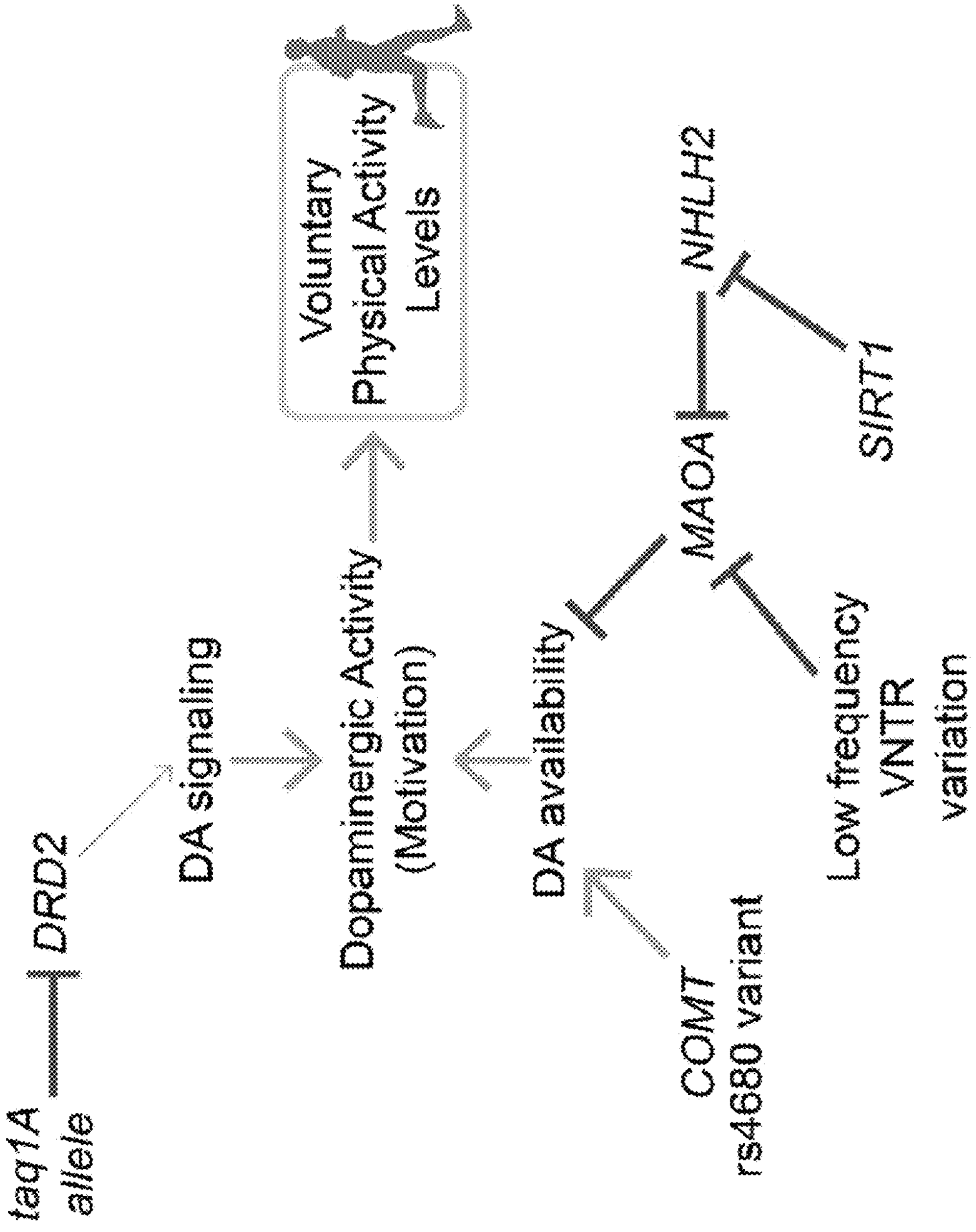
FIG. 11 is a diagram depicting dopaminergic related genes.

Effects of Transcranial Direct Current Stimulation on Physical Activity in Healthy Subjects: A Pilot Study Introduction Physical activity (PA) has well-established health benefits. Current efforts to enhance PA have targeted mainly socioeconomic factors. Despite these efforts, only a small number of adults engages in regular PA. Regulation of voluntary PA is linked to brain biological mechanisms involving the dopaminergic system. There is extensive evidence in rodents and humans that associates dopaminergic systems with PA behavior (See FIGS. 10 and 11). Detailed review on the role of dopaminergic systems in regulating PA levels was done by Ruiz-Tejada and colleagues (Ruiz-Tejada A, Neisewander J, Katsanos C S. Brain Sciences. 2022; 12(3):333). Transcranial direct current stimulation (tDCS) involves neuromodulation and it has been shown that when applied to the dorsolateral prefontal cortex tDCS can increase extracellular dopamine levels in humans (Fonteneau et al., Cereb Cortex. 2018; 28(7):2636-46).

Purpose

To determine if tDCS targeted to the left dorsolateral prefrontal cortex and coupled to an exercise stimulus increases overall daily PA in healthy subjects.

Methods

Figure 12:
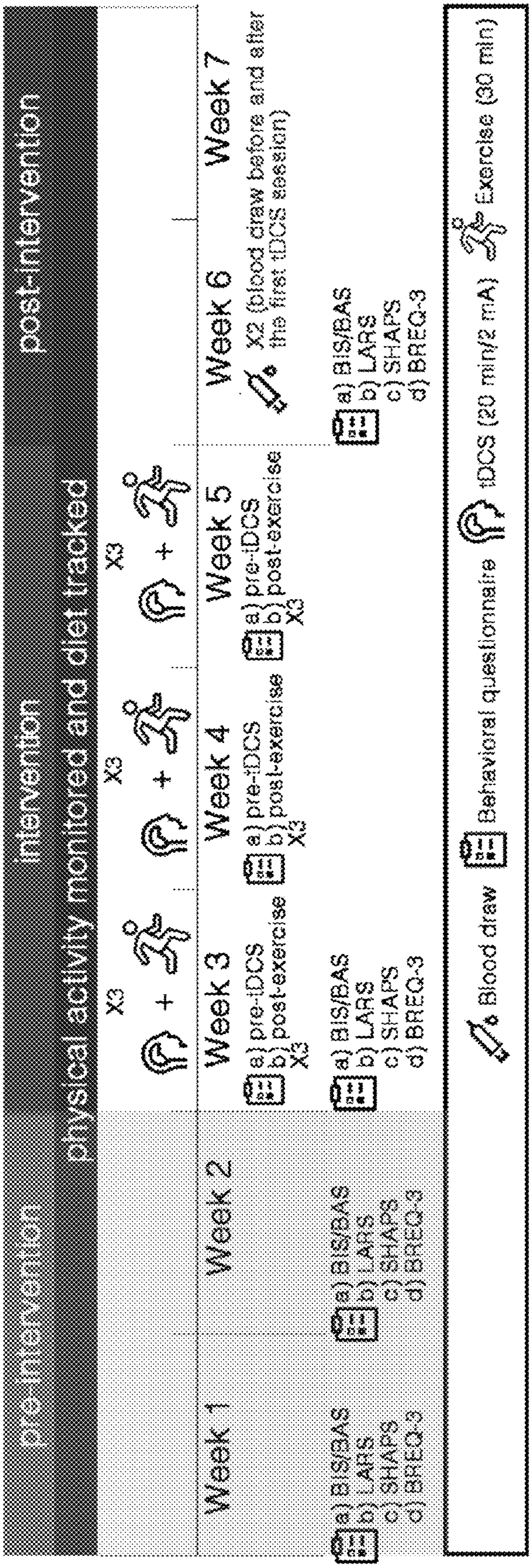
FIG. 12 is a diagram depicting the study design for the Effects of Transcranial Direct Current Stimulation on Physical Activity in Healthy Subjects.
Figure 14:
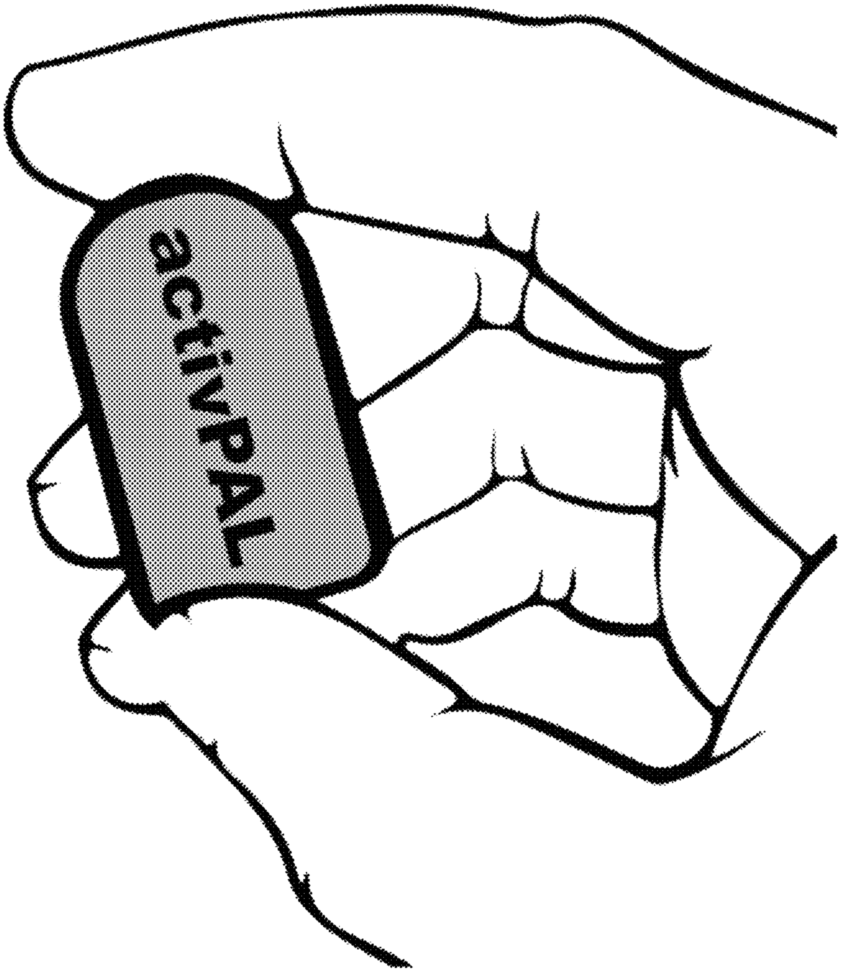
FIG. 14 is a an abstracted illustration depicting the size and shape of a conventional biometric device "activPAL" used in a study for tracking activity levels.
Figure 15:
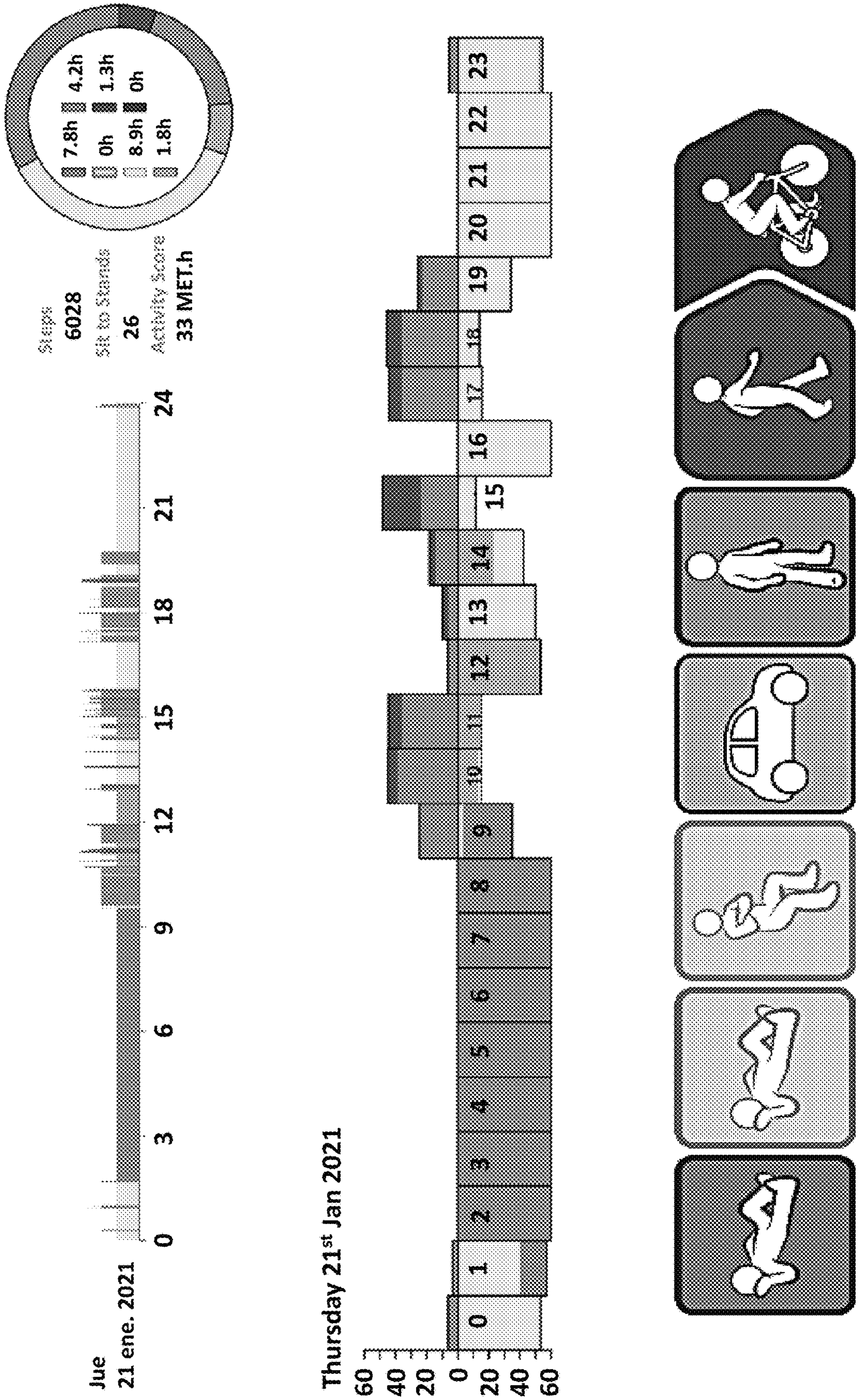
FIG. 15 depicts exemplary processed data output from the biometric device "activPAL".

In a single-blinded parallel design, subjects were randomly assigned to a group undergoing Active (n=13) (mean±SD; age=26.8±10.2 years; 3 males, 10 females) or Sham/control (n=9) (age=23.3±7.9 years; 2 males, 7 females) tDCS. The schedule of the study is displayed in FIG. 12. A subject with electrodes stimulating the left dorsolateral prefrontal cortex is displayed in FIG. 13. PA was monitored using a thigh-worn activPAL micro accelerometer (FIG. 14) for 2 weeks before (PRE) and 3 weeks during (DUR) the tDCS intervention. The tDCS intervention consisted of 20 mins of tDCS (ie. active or sham), followed by brisk walking for 30 mins, 3 times a week during DUR. Shown in FIG. 15 are recording of physical activity using the activPAL micro accelerometer. PA was evaluated as Total Daily Steps (TDS) and Activity Score (AS; describing PA energy expenditure in terms of metabolic equivalent (MET)). Collected data corresponding to PRE and DUR were averaged for the course of week 2 and 3, respectively.

Results

Figure 16:
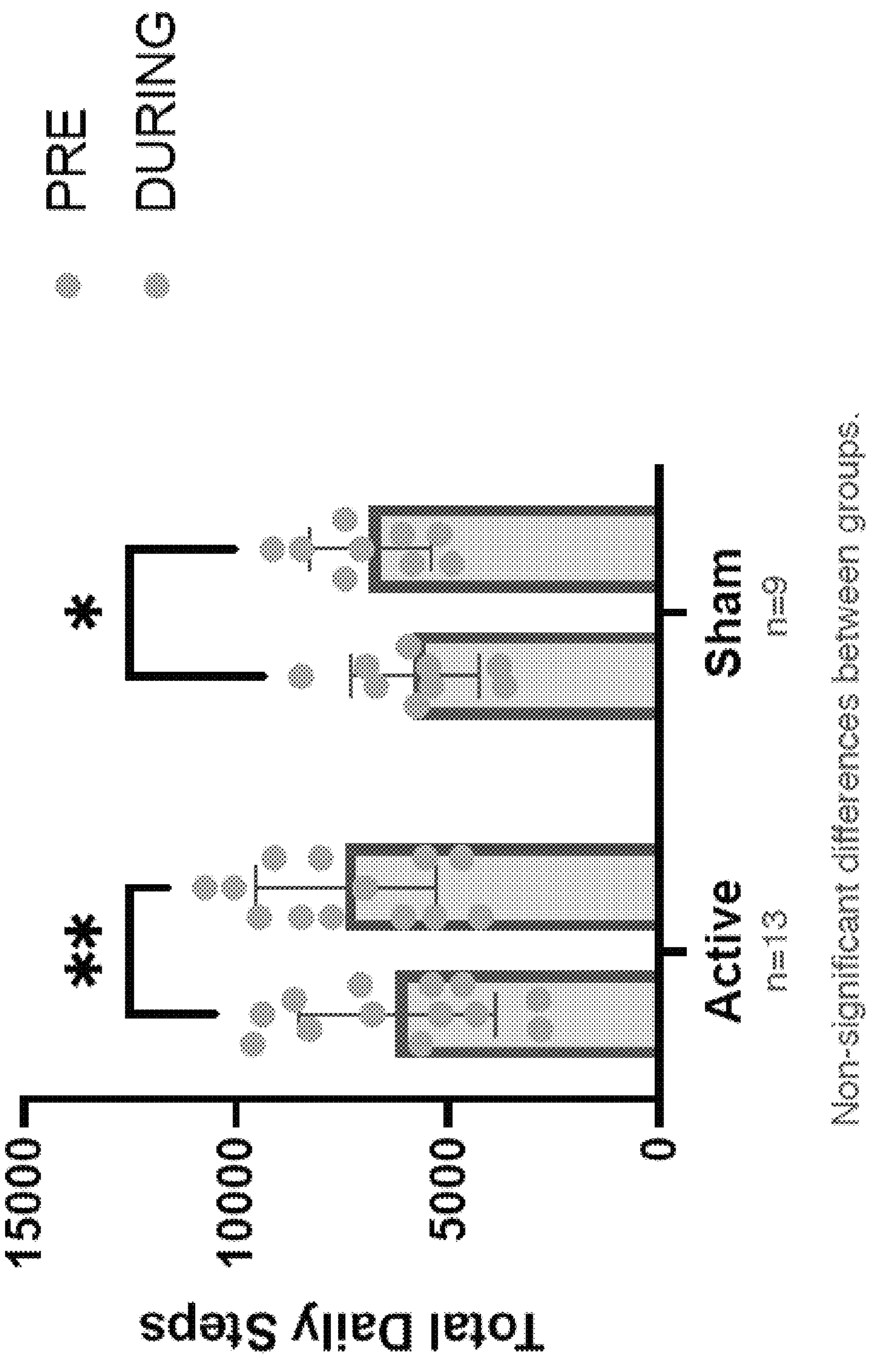
FIG. 16 depicts the Total Daily Steps (TDS) results for a study of TDS vs a Study Group having tDCS administered prior to and during physical activity.
Figure 17:
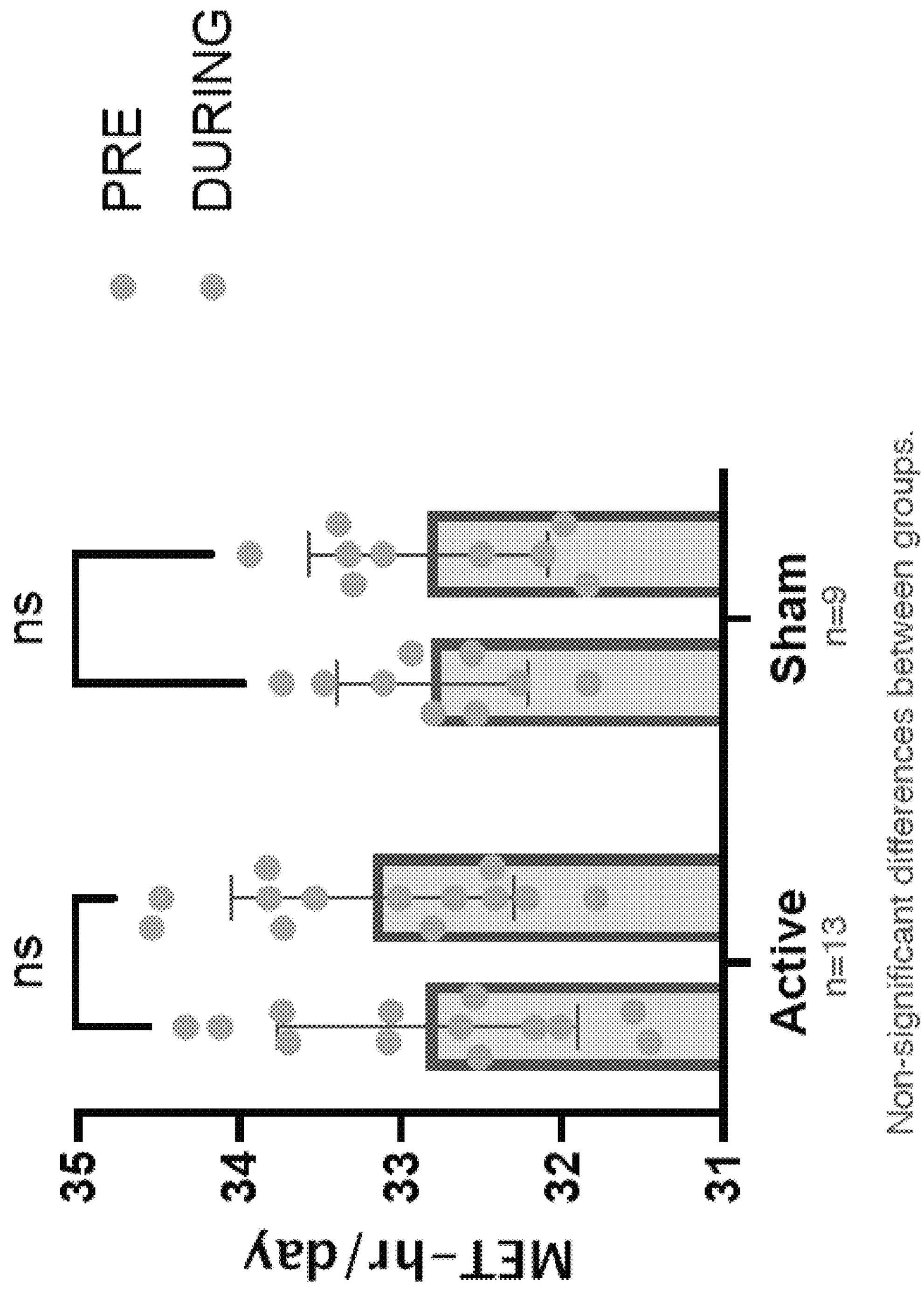
FIG. 17 depicts the Activity Score (AS) results for a study of Metabolic Equivalent (MET) hr/day vs a Study Group having tDCS administered prior to and during physical activity.

ANOVA analyses found significant effects for time for Total Daily Steps (TDS) (P<shown in FIG. 16, but not for Activity Score (AS) (P>0.05), as shown in FIG. 17. Pairwise comparisons indicated no significant effects for neither TDS or AS at PRE. TDS (steps) increased in response to the tDCS, in both the Active (DUR, 7411±2126 vs PRE, 6201±2303; P<0.01) and the Sham (DUR, 6840±1443 vs PRE, 5778±1508; P<0.05) groups. However, TDS response was ~14% higher in the Active Group. AS (MET-hr/day) increased in response to the tDCS in the Active (DUR, 33.2±0.9 vs PRE, 32.8±0.9 steps; P≤0.05), but not Sham (DUR, 32.8±0.8 vs PRE, 32.8±0.6 steps; P>0.05) group.

Conclusion

Three weeks of active tDCS increases measures of daily PA in healthy subjects. Although studies with larger number of subjects are needed, this study provides preliminary evidence for neurostimulation as a promising intervention to increase PA in healthy adults.

Preliminary Report of Results on the Use of tDCS Coupled with Exercise to Enhance Physical Activity Behavior This study was a parallel, single blinded and randomized (70/30) control trial. A total of 65 participants were assigned to the active tDCS (a-tDCS) or sham (sham-tDCS) group. However, participants who dropped out of the study within the first three weeks (n=25) and had more than 10 days of missing data during the intervention period due to a lost activity tacker (n=1), who were left-handed (n=2), and currently taking any medication that directly interacts with the 5-HT, GLU and DA pathways and consumed daily stimulants (e.g., Adderall and caffeine 5-10 mg/kg) (n=5) were excluded from the study. The final sample size that was analyzed included 21 participants in the active-tDCS (a-tDCS) group (age 23.41±7.65 years old; 61.9% female) and 11 in the sham-tDCS group (age 24.14±8.10 years old; 63.64% female).

The study consisted of 7 weeks. The first 2 weeks were for baseline measurement (BSL), during the following 3 weeks intervention took place (INT), and the last 2 weeks were a follow up period (FUP). Motivation for exercise was assessed using the BREQ-3 questionnaire. Scores in BREQ-3 were compared from BSL to INT. Physical activity (PA) was measured daily using activPAL micro accelerometers (steps/waking hours). PA was compared from BSL to INT and then from INT to FUP.

Motivation for Exercise

Figure 18:
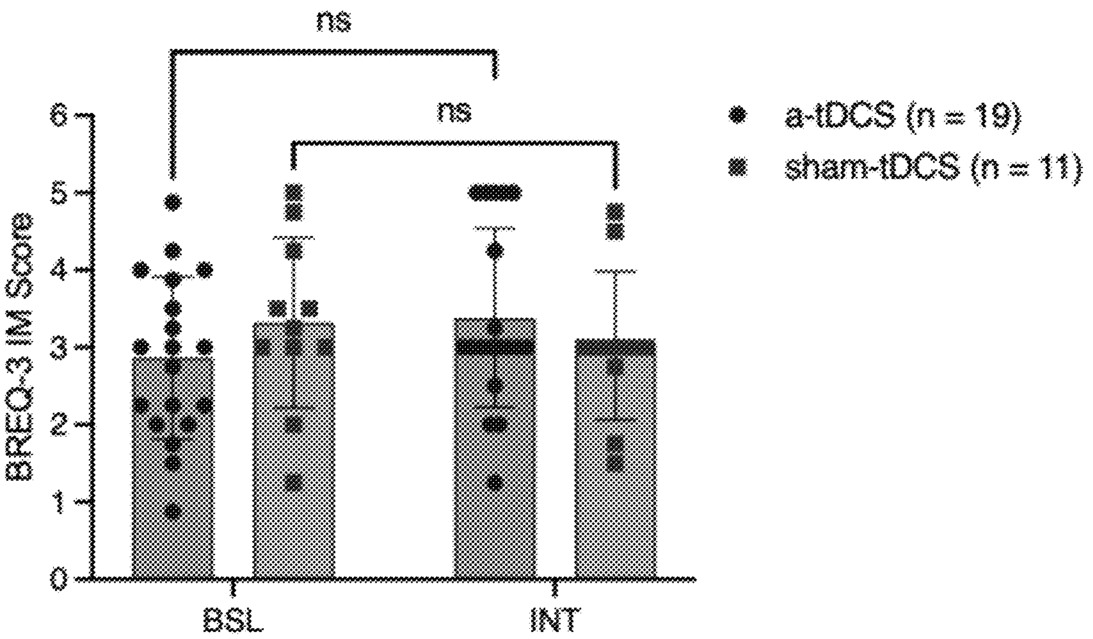
FIG. 18 depicts the BREQ-3 Intrinsic Motivation Scores comparison results as well as Repeated Measures, 2-way ANOVA, and Sidak's multiple comparisons test.

A repeated-measures 2-way ANOVA revealed a significant main effect of the interaction of time (BAS/INT) and group (F(1,28)=4.43, p=0.04). Sidak's multiple comparisons post hoc test was non-significant within groups. (See FIG. 18)

Physical Activity Initial Analysis

Figure 19B:
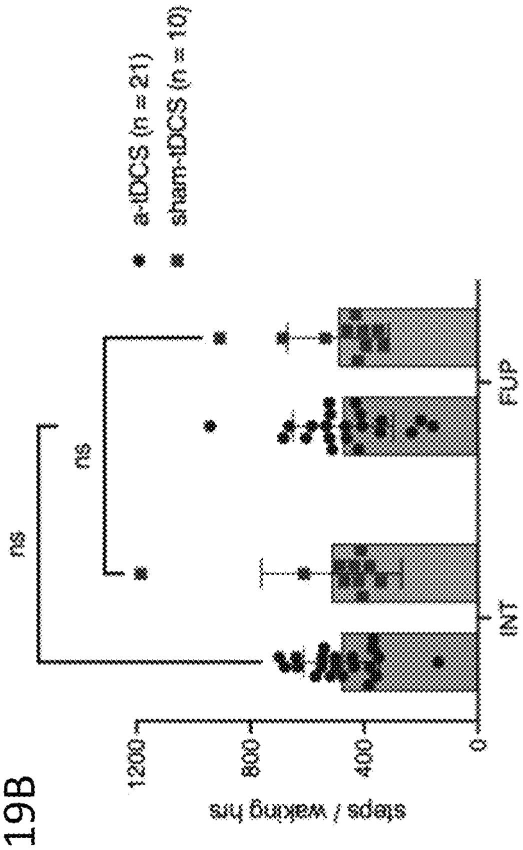
FIGS. 19A-19B depict the results for Repeated Measures, 2-way ANOVA and Sidak's multiple comparisons (GraphPad Prism v.9.5.1).
Figure 19A:
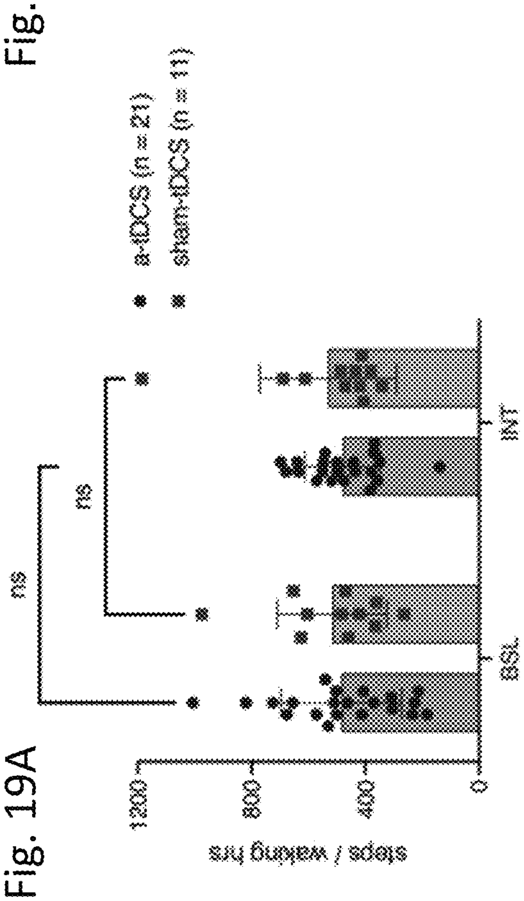

Initial results from a repeated-measures 2-way ANOVA revealed no significant differences in PA levels between groups (p>0.05). (See FIG. 19)

Figures 20A, 20B, 20C, 20D:
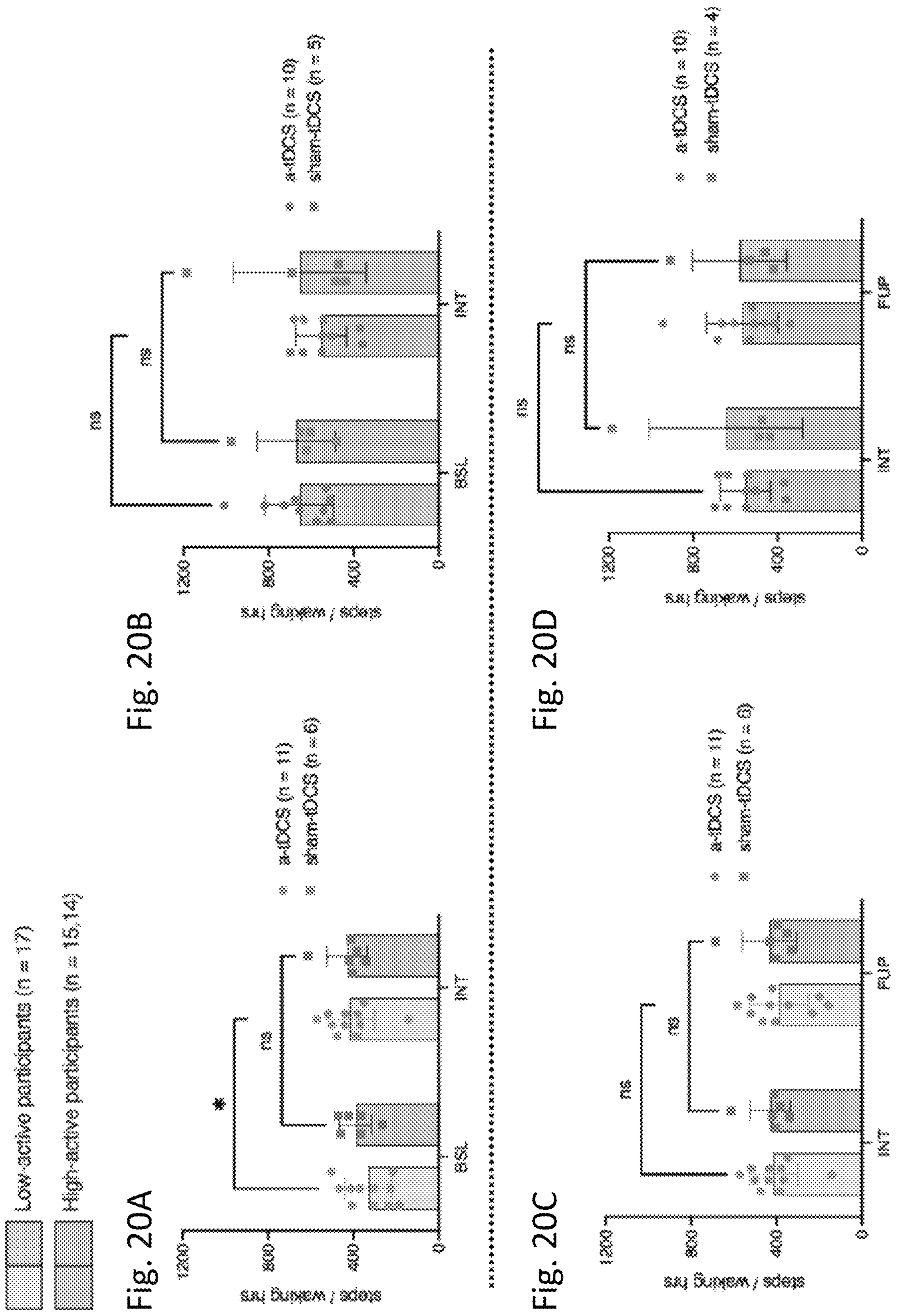
FIGS. 20A-20D depict the results for the Exploration by PA level. Repeated Measures, 2-way ANOVA and Sidak's multiple comparisons. *$P<0.05$.

Physical Activity Post-Hoc Exploratory Analysis: Participant Split by Physical Activity Level For this exploratory analysis, participants in both the a-tDCS and sham-tDCS groups were split into low-active and high-active participants. Classification of activity levels was made based on a median split of the BSL physical activity levels. (See FIG. 20)

For participants who were lower active and underwent a-tDCS, results of the repeated measures 2-way ANOVA revealed a significant main effect within subjects of transcranial direct current stimulation (tDCS) on physical activity levels from BAS to INT (F(1,15)=4.80, p<0.05). However, there were no interaction or between subjects effect. Sidak's multiple comparisons were conducted to further explore the main effects. In the low-active group, participants who received a-tDCS exhibited higher PA from BSL to INT as compared to those in the sham group (p<0.05). In the high-active participants group, there were no significant differences in physical activity levels between participants who received active tDCS and those who received sham tDCS (p>0.05).

Relationship Between Motivation and Physical Activity

Figure 21:
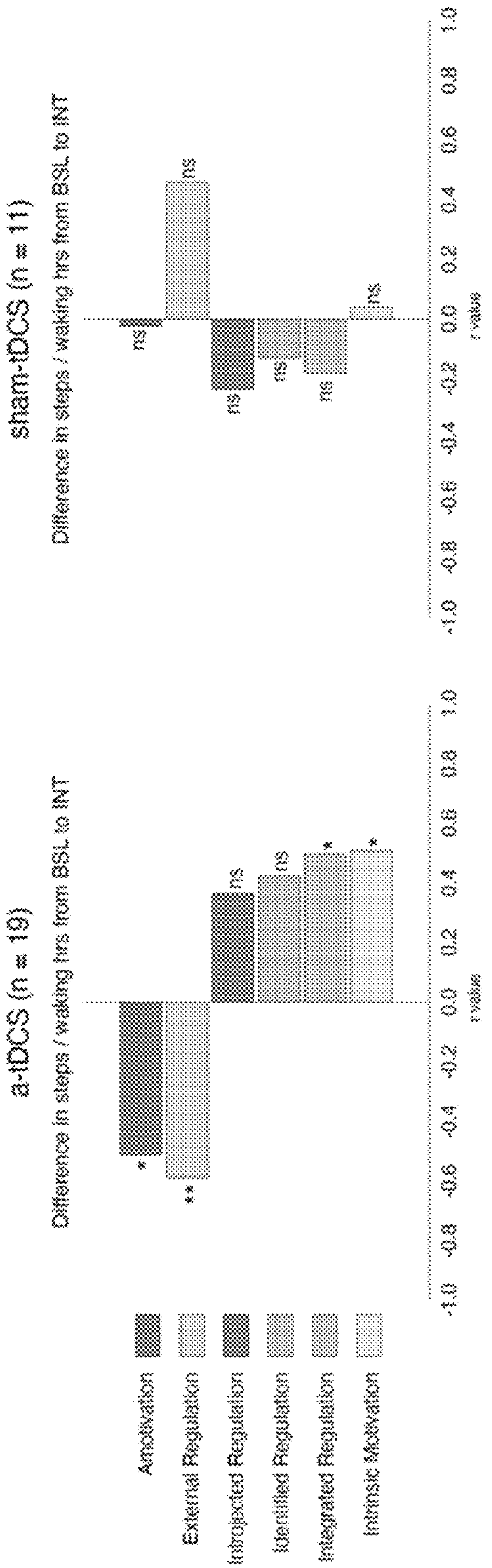
FIG. 21 depicts the results for Pearson's correlations for the relationship between the difference in PA from BSL to INT, and INT Intrinsic Motivation (IM) score. (*$P<0.05$, **$P<0.01$)

Pearson's correlations were computed to examine the relationships between the effect of tDCS on PA (difference from BAS to INT) and INT scores for all the BREQ-3 dimensions. In the a-tDCS group, results revealed significant positive correlations between Integrated Regulation and IM (IGR: r=0.50, p<0.05; IM: r=0.51, p<0.05) and negative correlations with Amotivation and External Regulation (A: r=−0.51, p<0.05; ER: r=−0.58, p<0.01). In contrast, no significant correlations were found in the sham group (p>0.05). (See FIG. 21)

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A device for positioning one or more neurostimulation electrodes on a subject, comprising:

an extendable headband comprising first and second arms each having a proximal end and a distal end, the two arms connected to one another at the proximal ends via an extension mechanism;

an electrode band having first and second ends, the first end rotatably connected by a first hinge to the first arm, and the second end rotatably connected by a second hinge to the second arm, wherein the electrode band rotates about an axis extending through the first hinge and the second hinge, and moves along a path on the sagittal plane; and first and second electrodes slidably positioned on the electrode band configured to deliver neurostimulation to the subject.

2. The device of claim 1, wherein the first and second electrodes are selected from flexible sponge electrodes, rubber electrodes, pad electrodes, or bare electrodes.

3. The device of claim 1, wherein the first electrode is an anode positioned in proximity to a first position on the head of the subject, and the second electrode is a cathode positioned in proximity to a second position on the head of the subject.

4. The device of claim 3, wherein the first position is the left dorsolateral prefrontal cortex, and the second position is the right dorsolateral prefrontal cortex.

5. The device of claim 1, wherein the device is configured to provide a stimulus to the subject to encourage physical activity.

6. The device of claim 1, wherein the device further comprises an activity sensor configured to track the activity of the subject.

7. The device of claim 1, wherein the electrodes connect to a neurostimulator device.

8. The device of claim 1, wherein the device further comprises a computing device with a power source.

9. A method of encouraging a behavior of a subject, comprising:

providing the device of claim 1;

positioning the first and second electrodes on the head of the subject; and providing neuromodulation or neurostimulation to the subject via the first and second electrodes.

10. The method of claim 9, wherein the method further comprises providing a stimulus to the subject related to the encouraged behavior.

11. The method of claim 9, wherein the first electrode is positioned in proximity to a first position on the head of the subject, and the second electrode is positioned in proximity to a second position on the head of the subject.

12. The method of claim 11, wherein the first position is the left dorsolateral prefrontal cortex, and the second position is the right dorsolateral prefrontal cortex.

13. The device of claim 1, wherein the extension mechanism adjusts a width of the device on the frontal plane.

14. The device of claim 1, wherein the first and second electrodes are slideable relative to the electrode band.

15. The device of claim 1, wherein the first hinge and the second hinge are configured to selectively lock the electrode band at one or more rotational positions about the axis, and wherein the electrode band comprises one or more sensors for determining the position of the electrode band relative to the headband.

16. A method of encouraging a behavior of a subject, comprising:

positioning a head-mounted device comprising a headband and an electrode band on the head of the subject, wherein the electrode band is rotatably connected by a first hinge and a second hinge to the headband such that the electrode band rotates about an axis extending through the first hinge and the second hinge, and moves along a path on the sagittal plane, and wherein the electrode band is configured to position one or more electrodes in contact with the head of the subject;

providing a stimulus to the subject related to the behavior;

providing neuromodulation or neurostimulation to the subject via the one or more electrodes in conjunction with the stimulus.

17. The method of claim 16, wherein the electrodes are positioned over the right and left dorsolateral prefrontal cortex.

18. The method of claim 17, wherein the neuromodulation or neurostimulation comprises a transcranial direct current stimulation (tDCS).

19. The method of claim 18, wherein the tDCS comprises an applied current of 1-6 mA for a duration of 1-45 minutes.

20. The method of claim 16, wherein the stimulus comprises an audio or visual stimulus.

21. The method of claim 16, wherein the stimulus comprises a representation of the subject executing aerobic or resistance exercise, and wherein the behavior is increased physical activity.

22. The method of claim 16, further comprising adjusting at least one dimension of the head-mounted device to conform to the size of the subject's head.

* * * * *